US009949831B2

(12) United States Patent
Keogh et al.

(10) Patent No.: US 9,949,831 B2
(45) Date of Patent: Apr. 24, 2018

(54) IMAGE-GUIDED HEART VALVE PLACEMENT

(71) Applicant: Medtronic, Inc., Minneapolis, MN (US)

(72) Inventors: James R. Keogh, Maplewood, MN (US); Timothy R. Ryan, Shorewood, MN (US); Carol E. Eberhardt, Fullerton, CA (US); Mark T. Stewart, Minneapolis, MN (US); James R. Skarda, Lake Elmo, MN (US); Timothy G. Laske, Shoreview, MN (US); Alexander J. Hill, Blaine, MN (US); Jack D. Lemmon, St. Paul, MN (US); David E. Francischelli, Anoka, MN (US)

(73) Assignee: Medtronics, Inc., Minneapolis, MN (US)

(*) Notice: Subject to any disclaimer, the term of this patent is extended or adjusted under 35 U.S.C. 154(b) by 176 days.

(21) Appl. No.: 14/174,268

(22) Filed: Feb. 6, 2014

(65) Prior Publication Data

US 2014/0221823 A1    Aug. 7, 2014

Related U.S. Application Data

(63) Continuation of application No. 13/585,622, filed on Aug. 14, 2012, now abandoned, which is a
(Continued)

(51) Int. Cl.
*A61F 2/24*    (2006.01)
*A61B 5/00*    (2006.01)
(Continued)

(52) U.S. Cl.
CPC .......... *A61F 2/2496* (2013.01); *A61B 5/0044* (2013.01); *A61B 5/1076* (2013.01);
(Continued)

(58) Field of Classification Search
CPC ...... A61B 18/1442; A61B 2017/00243; A61B 2018/00291; A61B 2018/00351;
(Continued)

(56) References Cited

U.S. PATENT DOCUMENTS 3,409,013 A    11/1968 Berry
3,540,431 A    11/1970 Mobin-Uddin
(Continued)

FOREIGN PATENT DOCUMENTS

DE    195 32 846    3/1997
DE    195 46 692    6/1997
(Continued)

OTHER PUBLICATIONS

Merriam-Webster dictionary definition of "Via" acquired on-line Oct. 31, 2016.*
(Continued)

*Primary Examiner* — Ruth S Smith
(74) *Attorney, Agent, or Firm* — Dicke, Billig, & Czaja, PLLC

(57) ABSTRACT

A method for determining whether a medical device is appropriate for implanting into a cardiovascular conduit of a patient is disclosed comprising imaging a first section of the conduit of the patient into which the medical device is to be implanted during a first expanded state occurring at a first portion of a heart rhythm; reimaging the first section of the conduit of the patient during a first contracted state occurring at a second portion of the heart rhythm; deriving, from the imaging and the reimaging, dimensional characteristics of the first section of the conduit; and determining whether
(Continued)

the medical device is appropriate for implantation in the first section of conduit based on the derived dimensional characteristics. The first section of the conduit includes a sizing device providing a selected radial force on the patient.

22 Claims, 14 Drawing Sheets

Related U.S. Application Data continuation of application No. 12/570,888, filed on Sep. 30, 2009, now Pat. No. 8,241,274, which is a continuation-in-part of application No. 11/298,282, filed on Dec. 9, 2005, now Pat. No. 8,221,402, which is a continuation-in-part of application No. 11/128,686, filed on May 13, 2005, now Pat. No. 7,706,882, which is a continuation-in-part of application No. 10/464,213, filed on Jun. 18, 2003, now Pat. No. 6,936,046, which is a continuation of application No. 09/629,194, filed on Jul. 31, 2000, now Pat. No. 6,595,934, which is a continuation-in-part of application No. 09/487,705, filed on Jan. 19, 2000, now abandoned, said application No. 11/128,686 is a continuation-in-part of application No. 10/156,315, filed on May 28, 2002, now Pat. No. 7,507,235, which is a continuation of application No. 09/879,294, filed on Jun. 12, 2001, now Pat. No. 6,447,443, said application No. 11/128,686 is a continuation-in-part of application No. 10/643,299, filed on Aug. 19, 2003, now Pat. No. 7,338,434.

(60) Provisional application No. 61/194,783, filed on Sep. 30, 2008, provisional application No. 60/571,182, filed on May 14, 2004, provisional application No. 60/261,343, filed on Jan. 13, 2001, provisional application No. 60/263,739, filed on Jan. 24, 2001, provisional application No. 60/282,029, filed on Apr. 6, 2001, provisional application No. 60/286,952, filed on Apr. 26, 2001, provisional application No. 60/424,243, filed on Nov. 6, 2002, provisional application No. 60/404,969, filed on Aug. 21, 2002.

(51) Int. Cl.
| | | |
|---|---|---|
| *A61B 5/107* | (2006.01) | |
| *A61B 8/00* | (2006.01) | |
| *A61N 7/02* | (2006.01) | |
| *A61B 18/14* | (2006.01) | |
| *A61B 17/00* | (2006.01) | |
| *A61B 18/00* | (2006.01) | |
| *A61B 34/20* | (2016.01) | |
| *A61B 90/00* | (2016.01) | |

(52) U.S. Cl.
CPC ............ *A61B 5/6853* (2013.01); *A61B 8/445* (2013.01); *A61B 34/20* (2016.02); *A61B 90/37* (2016.02); *A61B 90/39* (2016.02); *A61F 2/2433* (2013.01); *A61N 7/02* (2013.01); *A61B 18/1442* (2013.01); *A61B 2017/00243* (2013.01); *A61B 2018/00291* (2013.01); *A61B 2018/00351* (2013.01); *A61B 2018/00577* (2013.01); *A61B 2034/2051* (2016.02); *A61B 2034/2063* (2016.02); *A61B 2090/378* (2016.02); *A61B 2090/397* (2016.02); *A61F 2210/009* (2013.01); *A61F 2250/0096* (2013.01)

(58) Field of Classification Search
CPC .. A61B 2018/00577; A61B 2034/2051; A61B 2034/2063; A61B 2090/378; A61B 2090/397; A61B 34/20; A61B 5/0044; A61B 5/1076; A61B 90/37; A61B 90/39; A61B 5/6853; A61B 8/445; A61F 2210/009; A61F 2250/0096; A61F 2/2433; A61F 2/2496; A61N 7/02
See application file for complete search history.

(56) References Cited

U.S. PATENT DOCUMENTS

| | | |
|---|---|---|
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |

(56) References Cited

U.S. PATENT DOCUMENTS

| | | |
|---|---|---|
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,749,890 A | 5/1998 | Shaknovich |
| 5,782,809 A | 7/1998 | Umeno et al. |
| 5,800,508 A | 9/1998 | Goicoechea et al. |
| 5,824,041 A | 10/1998 | Lenker et al. |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,629,534 B1 | 10/2003 | St. Goar et al. |
| 6,635,068 B1 | 10/2003 | Dubrul et al. |
| 6,652,571 B1 | 11/2003 | White et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B2 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,685,739 B2 | 2/2004 | Dimatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon et al. |
| 6,792,979 B2 | 9/2004 | Konya et al. |
| 6,797,002 B2 | 9/2004 | Spence et al. |
| 6,821,297 B2 | 11/2004 | Snyders |

(56) References Cited

U.S. PATENT DOCUMENTS

| | | |
|---|---|---|
| 6,830,575 B2 | 12/2004 | Stenzel et al. |
| 6,830,585 B1 | 12/2004 | Artof et al. |
| 6,846,325 B2 | 1/2005 | Liddicoat |
| 6,866,650 B2 | 3/2005 | Stevens et al. |
| 6,872,223 B2 | 3/2005 | Roberts et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,201,761 B2 | 4/2007 | Woolfson et al. |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,335,218 B2 | 2/2008 | Wilson et al. |
| 7,338,520 B2 | 3/2008 | Bailey et al. |
| 7,374,571 B2 | 5/2008 | Pease et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn |
| 7,556,646 B2 | 7/2009 | Yang et al. |
| 2001/0002445 A1 | 3/2001 | Vesely |
| 2001/0001314 A1 | 5/2001 | Davison et al. |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0071518 A1 | 6/2002 | Bruder et al. |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | MacOviak et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Sequin et al. |
| 2004/0097788 A1 | 5/2004 | Mourles et al. |
| 2004/0098112 A1 | 5/2004 | DiMatteo et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty et al. |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson et al. |
| 2004/0167620 A1 | 8/2004 | Ortiz et al. |
| 2004/0193261 A1 | 9/2004 | Berreklouw |
| 2004/0210240 A1 | 10/2004 | Saint |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0225353 A1 | 11/2004 | McGuckin, Jr. |
| 2004/0225354 A1 | 11/2004 | Allen et al. |
| 2004/0254636 A1 | 12/2004 | Flagle et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | MacOviak et al. |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1 | 4/2005 | Cali |
| 2005/0075712 A1 | 4/2005 | Biancucci et al. |

(56) References Cited

U.S. PATENT DOCUMENTS

| | | |
|---|---|---|
| 2005/0075717 A1 | 4/2005 | Nguyen |
| 2005/0075719 A1 | 4/2005 | Bergheim |
| 2005/0075724 A1 | 4/2005 | Svanidze et al. |
| 2005/0075727 A1 | 4/2005 | Wheatley |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua et al. |
| 2005/0119688 A1 | 6/2005 | Berheim |
| 2005/0131438 A1 | 6/2005 | Cohn |
| 2005/0137686 A1 | 6/2005 | Salahieh et al. |
| 2005/0137692 A1 | 6/2005 | Haug et al. |
| 2005/0137701 A1 | 6/2005 | Salahieh et al. |
| 2005/0148997 A1 | 7/2005 | Valley et al. |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203618 A1 | 9/2005 | Sharkawy et al. |
| 2005/0222674 A1 | 10/2005 | Paine |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0009841 A1 | 1/2006 | McGuckin et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0247763 A1 | 11/2006 | Slater |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heynicnck-Janitz et al. |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi et al. |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan et al. |
| 2008/0065001 A1 | 3/2008 | Dinucci et al. |
| 2008/0065206 A1 | 3/2008 | Liddicoat |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154356 A1 | 6/2008 | Obermiller et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0262593 A1 | 10/2008 | Ryan et al. |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0138079 A1 | 5/2009 | Tuval et al. |
| 2009/0164004 A1 | 6/2009 | Cohn |
| 2009/0171447 A1 | 7/2009 | Vonseggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0240264 A1 | 9/2009 | Tuval et al. |
| 2009/0240320 A1 | 9/2009 | Tuval et al. |
| 2010/0016958 A1 | 1/2010 | St. Goar et al. |

FOREIGN PATENT DOCUMENTS

| | | |
|---|---|---|
| DE | 198 57 887 | 7/2000 |
| DE | 199 07 646 | 8/2000 |
| DE | 100 48 814 | 9/2000 |
| DE | 100 49 812 | 4/2002 |

(56) References Cited

FOREIGN PATENT DOCUMENTS

| | | |
|---|---|---|
| DE | 100 49 813 | 4/2002 |
| DE | 100 49 815 | 4/2002 |
| EP | 0103546 | 3/1984 |
| EP | 0850607 | 7/1998 |
| EP | 1057459 | 6/2000 |
| EP | 1057460 | 6/2000 |
| EP | 1088529 | 4/2001 |
| EP | 1340473 | 9/2003 |
| EP | 093743981 | 9/2003 |
| EP | 0819013 | 6/2004 |
| FR | 2788217 | 12/1999 |
| GB | 2056023 | 3/1981 |
| SU | 1271508 | 11/1986 |
| TK | 05/004753 | 1/2005 |
| WO | 91/017720 | 11/1991 |
| WO | 93/001768 | 2/1993 |
| WO | 95/29640 | 11/1995 |
| WO | 98/14137 | 4/1998 |
| WO | 98/29057 | 7/1998 |
| WO | 99/033414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 04/019811 | 3/2004 |
| WO | 04/019825 | 3/2004 |
| WO | 04/023980 | 3/2004 |
| WO | 04/041126 | 5/2004 |
| WO | 04/058106 | 7/2004 |
| WO | 04/089250 | 10/2004 |
| WO | 05/027790 | 3/2005 |
| WO | 05/046528 | 5/2005 |
| WO | 08/100599 | 8/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |

OTHER PUBLICATIONS

U.S. Appl. No. 12/250,163, filed Oct. 13, 2008.
U.S. Appl. No. 61/192,199, filed Sep. 15, 2008.
U.S. Appl. NO. 12/253,858, filed Oct. 17, 2008.
U.S. Appl. No. 12/596,343, filed Apr. 14, 2008.
U.S. Appl. No. 61/129,170, filed Jun. 9, 2008.
Andersen et al, "Transluminal implantation of artificial heart valves. Description of a new expandable aortic valve and initial results with implantation by catheter technique in closed chest pigs." Euro. Heart J. (1992) 13:704-708.
Babaliaros et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. IL Second edition. WB Saunders, Philadelphia, 1994:1268-1276.
Bonhoeffer et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer et al, "Technique and Results of Percutaneous Mitral Valvuloplasty With the Multi-Track System," Journal ofInterventional Cardiology (United States), 13(4):263-268 (Aug. 2000).
Bonhoeffer et al, "Transcatheter Implantation of a Bovine Valve in Pulmonary Position: A Lamb Study," Circulation (United States), Aug. 15, 2000, pp. 813-6.
Boudjemline et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline et al, "Percutaneous Implantation of a Biological Valve in Aortic Position: Preliminary Results in a Sheep Study," European Heart Journal 22, Sep. 2001, p. 630.
Boudjemline et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline et al, "Percutaneous Valve Insertion: A New Approach," Journal of Thoracic and Cardiovascular Surgery (United States), Mar. 2003, pp. 741-743.
Boudjemline, et al, "Steps Toward Percutaneous Aortic Valve Replacement," Circulation (United States), Feb. 12, 2002, pp. 775-778.
Boudjemline et al, "Transcatheter Reconstruction of the Right Heart," Cardiology in the Young (England), Jun. 2003, pp. 308-311.
Commeau et al, "Percutaneous balloon dilatation of calcific aortic valve stenosis: anatomical and haemodynamic evaluation," 1988, British Heart Journal, 59:227-238.
Cribier et al, "Percutaneous Transcatheter Implantation of an Aortic Valve Prosthesis for Calcific Aortic Stenosis: First Human Case Description," Circulation (2002) 3006-3008.
Davidson et al, "Percutaneous therapies for valvular heart disease," Cardiovascular Pathology 15 (2006) 123-129.
Hanzel et al., "Complications of percutaneous aortic valve replacement: experience with the Criber-Edwards™ percutaneous heart valve," EuroIntervention Supplements (2006), 1 (Supplement A) A3-A8.
Huber et al., "Do Valved Stents Compromise Coronary Flow?" Eur. J. Cardiothorac. Surg. 2004;25:754-759.
Khambadkone et al, "Percutaneous Pulmonary Valve Implantation: Impact of Morphology on Case Selection," Circulation 108 (17 Sunnlement), Oct. 28, 2003, p. IV-642-IV-643.
Medtech Insight, "New Frontiers in Heart Valve Disease," 7(8): 226-260 (2005).
Ruiz, "Transcathether Aortic Valve Implantation and Mitral Valve Repair: State of the Art," Pediatric Cardiology, 26(3):289-294 (2005).
Stassano et al., "Mid-term results of the valve-on-valve technique for bioprosthetic failure," Eur. J. Cardiothorac. Surg. 2000; 18:453-457.
Webb et al, "Percutaneous Aortic Valve Implantation Retrograde from the Femoral Artery," Circulation (2006), 113;842-850.
Yonga et al, "Percutaneous Balloon Mitral Valvotomy: Initial Experience in Nairobi Using a New Multi-Track Catheter System," East African Medical Journal (Kenya), Feb. 1999, pp. 71-74.

(56) References Cited

OTHER PUBLICATIONS

Yonga et al, "Percutaneous Transvenous Mitral Commissurotomy in Juvenile Mitral Stenosis," East African Medical Journal (Kenya), Apr. 2003, pp. 172-174.
Expert report of Dr. Nigel Buller, dated Jan. 12, 2009, Edwards' United Kingdom action for invalidity, Claim No. HC 08C00934 (83 pages).
Expertreport ofDr.Nigel Buller, non-confidential annex-infringement, dated Jan. 12, 2009, Edwards' United Kingdom action for invalidity, ClaimNo. HC 08C00934 (95 pages).
Expert report of Dr. Rodolfo Quijano, dated Jan. 9, 2009, Edwards' United Kingdom action for invalidity, Claim No. HC 08C00934 (18 pages).
First Expert report of Prof. David Williams, dated Jan. 12, 2009, Edwards' United Kingdom action for invalidity, Claim No. HC 08C00934 (41 pages).
First Expert report of Prof. Martin Rothman, dated Jan. 12, 2009, Edwards' United Kingdom action for invalidity, Claim No. HC 08C00934 (64 pages).
Fourth Expert report of Prof. Martin Rothman, dated Apr. 22, 2009, Edwards' United Kingdom action for invalidity, Claim No. HC 08C00934 (10 pages).
Second Expert report of Dr. Nigel Buller, dated Feb. 25, 2009, Edwards' United Kingdom action for invalidity, Claim No. HC 08C00934 (24 pages).
Second Expert report of Dr. Rodolfo Quijano, dated Feb. 26, 2009, Edwards' United Kingdom action for invalidity, Claim No. HC 08C00934 (6 pages).
Second Expert report of Prof. David Williams, dated Feb. 5, 2009, Edwards' United Kingdom action for invalidity, Claim No. HC 08C00934 (15 pages).
Second Expert report of Prof. Martin Rothman, dated Feb. 5, 2009, Edwards' United Kingdom action for invalidity, Claim No. HC 08C00934 (11 pages).
Third Expert report of Dr. Nigel Buller, dated Apr. 21, 2009, Edwards' United Kingdom action for invalidity, Claim No. HC 08C00934 (6 pages).
Third Expert report of Dr. Rudolfo Quijano, dated Apr. 27, 2009, Edwards' United Kingdom action for invalidity, Claim No. HC 08C00934 (3 pages).
Third Expert report of Prof. David Williams, dated Apr. 22, 2009, Edwards' United Kingdom action for invalidity, Claim No. HC 08C00934 (9 pages).
First Expert report of Dr. Nigel Person Buller (30 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (30 pages).
Second Expert report of Dr. Nigel Person Buller (5 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (Jun. 18, 2008).
Drawing by Dr. Buller (Edwards Expert) of his interpretation of the "higher stent" referred to at col. 8, lines 13-222 of Andersen EP 592410B1 (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of "higher stent" on the schematic representation of the aortic valve area set out in Figure 2 of Rothman's first expert report (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Professor John R. Pepper (20 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (Apr. 28, 2008).
Second Expert report of Professor John R. Pepper (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (Jun. 10, 2008).
First Expert report of Dr. Anthony C. Lunn (7 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (Apr. 28, 2008).
First Witness statement of Stanton Rowe (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (May 27, 2008).
Second Witness statement of Stanton Rowe (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (Jun. 20, 2008).
PVT slides naming Alain Cribier, Martin Leon, Stan Rabinovich and Stanton Rowe (16 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Professor Martin Terry Rothman (75 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (Apr. 28, 2008).
Reply Expert report of Professor Martin Terry Rothman (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (May 27, 2008).
First Expert report of Richard A. Hillstead (41 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (Apr. 28, 2008).
Reply Expert report of Richard A. Hillstead (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243 (May 27, 2008).
Block et al., "Percutaneous Approaches to Valvular Heart Disease," Current Cardiology Reports, vol. 7 (2005) pp. 108-113.
Bonhoeffer et al, "Percutaneous Insertion of the Pulmonary Valve," Journal of the American College of Cardiology (United States), May 15, 2002, pp. 1664-1669.
Bonhoeffer et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.
Boudjemline et al, "Images in Cardiovascular Medicine. Percutaneous Aortic Valve Replacement in Animals," Circulation (United States), Mar. 16, 2004, 109, p. e161.
Boudjemline et al, "Percutaneous Aortic Valve Replacement: Will We Get There?" Heart (British Cardiac Society) (England), Dec. 2001, pp. 705-706.
Boudjemline et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline et al, "The Percutaneous Implantable Heart Valve," Progress in Pediatric Cardiology (Ireland), 2001, pp. 89-93.
Coats et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Khambadkone, "Nonsurgical Pulmonary Valve Replacement: Why, When, and How?" Catheterization and Cardiovascular Interven-

(56) References Cited

OTHER PUBLICATIONS tions-Official Journal of the Society for Cardiac Angiography & Interventions (United States), Jul. 2004, pp. 401-408.
Khambadkone et al, "Percutaneous Implantation of Pulmonary Valves," Expert Review of Cardiovascular Therapy (England), Nov. 2003, pp. 541-548.
Khambadkone et al, "Percutaneous Pulmonary Valve Implantation: Early and Medium Term Results," Circulation 108 (17 Supplement), Oct. 28, 2003, p. IV-375.
Lutter et al, "Percutaneous Aortic Valve Replacement: An Experimental Study. I. Studies on Implantation," The Journal of Thoracic and Cardiovascular Surgery, Apr. 2002, pp. 768-776.
Lutter et al, "Percutaneous Valve Replacement: Current State and Future Prospects," Annals of Thoracic Surgery (Netherlands), Dec. 2004, pp. 2199-2206.
Palacios, "Percutaneous Valve Replacement and Repair, Fiction or Reality?" Journal of American College of Cardiology, vol. 44, No. 8 (2004) pp. 1662-1663.
Saliba et al, "Treatment of Obstructions of Prosthetic Conduits by Percutaneous Implantation of Stents," Archives des Maldies du Coeur et des Vaisseaux (France), 1999, pp. 591-596.
Yonga et al, "Effect of Percutaneous Balloon Mitral Valvotomy on Pulmonary Venous Flow in Severe Mitral Stenosis," East African Medical Journal (Kenya), Jan. 1999, pp. 28-30.
Yonga et al, "Percutaneous Transluminal Balloon Valvuloplasty for Pulmonary Valve Stenosis: Report on Six Cases," East African Medical Journal (Kenya), Apr. 1994, pp. 232-235.
Pavcnik et al., "Aortic and venous valve for percutaneous insertion," Min. Invas. Ther. & Allied Techol. 2000, 9 (3/4):287-292.

\* cited by examiner

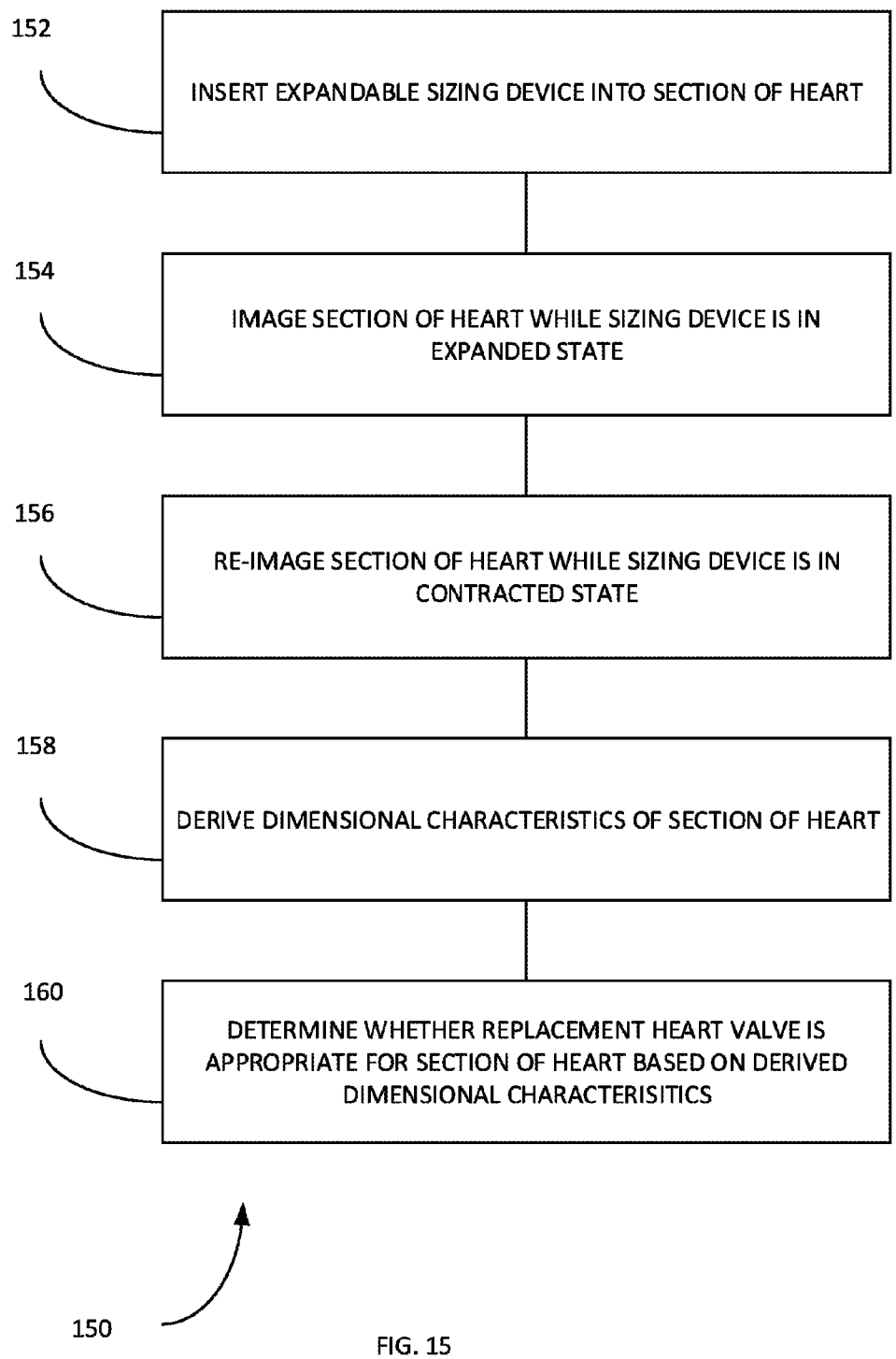

IMAGE-GUIDED HEART VALVE PLACEMENT

CROSS-REFERENCE TO RELATED SECTION

This application is a continuation of U.S. application Ser. No. 13/585,622, filed on Aug. 14, 2012, now abandoned, the contents of which are incorporated herein by reference.

U.S. patent application Ser. No. 13/585,622 is a continuation of U.S. application Ser. No. 12/570,888, filed on Sep. 30, 2009, now U.S. Pat. No. 8,241,274, the contents of which are incorporated herein by reference.

U.S. patent application Ser. No. 12/570,888 filed Sep. 30, 2009 claims the benefit of U.S. Provisional Patent Application Ser. No. 61/194,783 filed on Sep. 30, 2008, the disclosure of which is incorporated herein by reference in its entirety.

U.S. patent application Ser. No. 12/570,888 filed Sep. 30, 2009 is also a continuation-in-part of U.S. patent application Ser. No. 11/298,282 filed Dec. 9, 2005 now U.S. Pat. No. 8,221,402, which is a continuation-in-part of U.S. patent application Ser. No. 11/128,686 filed May 13, 2005 now U.S. Pat. No. 7,706,882.

U.S. patent application Ser. No. 11/128,686 filed May 13, 2005 claims the benefit of U.S. Provisional Patent Application Ser. No. 60/571,182 filed on May 14, 2004, the disclosure of which is incorporated herein by reference in its entirety.

U.S. patent application Ser. No. 11/128,686 filed May 13, 2005 is a continuation-in-part of U.S. patent application Ser. No. 10/464,213 filed Jun. 18, 2003, now U.S. Pat. No. 6,936,046, which is a continuation of U.S. patent application Ser. No. 09/629,194 filed Jul. 31, 2000, now U.S. Pat. No. 6,595,934, which is a continuation-in-part of U.S. patent application Ser. No. 09/487,705 filed Jan. 19, 2000, now abandoned, the disclosures of which are incorporated herein by reference in their entirety.

U.S. patent application Ser. No. 11/128,686 filed May 13, 2005 is also a continuation-in-part of U.S. patent application Ser. No. 10/156,315 filed May 28, 2002, now U.S. Pat. No. 7,507,235, which is a continuation of U.S. patent application Ser. No. 09/879,294 filed Jun. 12, 2001, now U.S. Pat. No. 6,447,443, which claims the benefit of the filing dates of U.S. Provisional Patent Application Ser. No. 60/261,343 filed Jan. 13, 2001, Ser. No. 60/263,739 filed Jan. 24, 2001, Ser. No. 60/282,029 filed Apr. 6, 2001 and Ser. No. 60/286,952 filed Apr. 26, 2001, the disclosures of which are incorporated herein by reference in their entirety.

U.S. patent application Ser. No. 11/128,686 filed May 13, 2005 is also a continuation-in-part of U.S. patent application Ser. No. 10/643,299 filed Aug. 19, 2003, now U.S. Pat. No. 7,338,434, which claims the benefit of the filing dates of U.S. Provisional Patent Application Ser. No. 60/424,243 filed Nov. 6, 2002 and Ser. No. 60/404,969 filed Aug. 21, 2002, the disclosures of which are incorporated herein by reference in their entirety.

TECHNICAL FIELD

The present disclosure relates generally to treatment of cardiac heart disease. More particularly, the present disclosure relates to implantable valve prostheses for implantation into the cardiac system.

BACKGROUND

Recently, there has been increasing interest in minimally invasive and percutaneous replacement of cardiac valves. Percutaneous replacement of a heart valve does not involve actual physical removal of the diseased or injured heart valve. Rather, the defective or injured heart valve typically remains in position while the replacement valve is inserted into a balloon catheter and delivered percutaneously via the vascular system to the location of the failed pulmonary valve. Such surgical techniques involve making a very small opening in the skin of the patient into which a valve assembly is inserted via a delivery device similar to a catheter. There, the replacement valve is expanded by the balloon to compress the native valve leaflets against the body opening in which it is inserted, anchoring and sealing the replacement valve. This technique is often preferable to more invasive forms of surgery, such as opening a large portion of the chest for cardiopulmonary bypass, for example.

In the context of percutaneous, pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is crimped or compressed around the balloon portion of a catheter until it is as close to the diameter of the catheter as possible. The valve is then delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits. Other implantables and implant delivery devices also are disclosed in published U.S. Pat. Application No. 2003/0036791 A1 and European Patent Application No. 1 057 460-A1.

Assignee's co-pending U.S. patent application titled "Apparatus for Treatment of Cardiac Valves and Method of Its Manufacture", filed Nov. 18, 2005 and assigned U.S. Ser. No. 11/282,275, describes percutaneous heart valves for use as a replacement pulmonary valve. Like the valves described by Tower et al., the heart valves of this co-pending application incorporate a valved segment of bovine jugular vein, mounted within an expandable stent.

In addition to percutaneous valve implantation, heart valve repair can also be accomplished using catheter-based valve repair procedures. In the context of annuloplasty ring implantation on a valve annulus, for example, a variety of repair procedures can be used, such as procedures that require indirect visualization techniques to determine the exact location of the heart valve and annuloplasty ring during placement of the ring at the valve annulus. Indirect visualization techniques, as described herein, are techniques that can be used for viewing an indirect image of body tissues and/or devices within a patient. One example of such a technique is referred to as endoscopic visualization, which involves displaying images from endoscopic light guides and cameras within the thoracic cavity on a video monitor that is viewed by a surgeon. Effective use of this method depends on having sufficient open space within the working area of the patient's body to allow the surgeon to recognize the anatomical location and identity of the structures viewed on the video display, which can be difficult to accomplish in certain areas of the heart.

Another indirect visualization technique involves the use of fluoroscopy, which is an imaging technique commonly used by physicians to obtain real-time images of the internal structures of a patient through the use of a fluoroscope. Fluoroscopy can be effective in many situations, but does have some drawbacks. For one example, some tissues, such as the cardiac tissues, do not readily appear under fluoroscopy, making it very difficult to accurately align an annuloplasty ring prior to its implantation. To improve the visualization of the area of interest, radiopaque contrast dye can be used with x-ray imaging equipment. However, when treating the mitral valve, for example, repeated injections of contrast dye are not practical because of rapid wash-out of the dye in this area of high fluid flow. For another example, to make high-volume contrast injections of this kind, an annuloplasty catheter system would require multiple lumens, undesirably large lumens, and/or an additional catheter, none of which is desirable during catheterization procedures. Further, multiple high-volume contrast injections are somewhat undesirable for the patient due to potential complications in the renal system, where the radiopaque contrast medium is filtered from the blood.

A wide variety of other techniques are available for viewing images of cardiac structures, including ultrasonography such as trans-thoracic echocardiography (TTE), trans-esophageal echocardiography (TEE), cardiac magnetic resonance (CMR) including magnetic resonance imaging (MRI) or magnetic resonance angiography (MRA), and computed tomography (CT) including computer tomography angiography (CTA). These techniques, used alone or in combination with other available techniques, all typically have certain drawbacks relative to visualization and guidance during catheter-based valve repair procedures.

Yet another visualization technique that can be used for catheter-based valve repair involves mapping a valve annulus, such as a mitral valve annulus, and obtaining real time imaging during heating heart surgery through the use of electromagnetic (EM) imaging and navigation. This type of technique can be effective for viewing the significant movement of the annulus during both systole and diastole that occurs during procedures performed on a beating heart. With EM navigation, a patient is generally placed on a table having a plurality of sensors either on the surface of the table or at positions around the table. The sensors are connected to a processor and the processor knows the positions of the sensors relative to the table. A patient is then placed on the table and immobilized, and then an elongated flexible device having at least three EM coils spaced along its distal portion can then be inserted into the patient's body (into the vascular system for example). The coils are typically made from extremely small diameter material that can be wound around the outside of the device or wound around an interior layer of the device and then covered with an additional layer of material. A very thin wire or some other electrically conductive material can be used to communicate from an external AC power source to each of these coils. Alternatively, wireless sensors can be used to eliminate the need to provide a wire to communicate with the EM coils.

As the elongated device is moved through the body, the sensors can detect the EM signal that is created by the moving coil. The processor then calculates the position of the coils relative to each sensor. The location of the sensors can be viewed on a display device, and the EM navigation can be combined with other navigation/visualization technologies so that the location of the EM coils in a patient's body can be viewed in real time. Additional sensors may also be incorporated into a system using EM navigation to improve the accuracy of the system, such as temporarily attaching sensors to a patient's body and/or covering at least a portion of a patient with a blanket that contains additional sensors. The relationship between all of the sensors can be used to produce the image of the patient's body on the table. Examples of methods and systems for performing medical procedures using EM navigation and visualization systems for at least part of an overall navigation and visualization system can be found, for example, in U.S. Pat. No. 5,782,765 (Jonkman); U.S. Pat. No. 6,235,038 (Hunter et al.); U.S. Pat. No. 6,546,271 (Resifeld); U.S. Patent Application No. 2001/0011175 (Hunter et al.); U.S. Patent Application No. 2004/0097805, (Verard et al.), and U.S. Patent Application No. 2004/0097806 (Hunter et al.), the entire contents of which are incorporated herein by reference.

Another method for mapping the mitral valve annulus and obtaining real time imaging during beating heart surgery is through the use of electro-potential navigation. Electro-potential (EP) navigation involves the use of external sensors that are placed on the patient. When using EP navigation, a low frequency electrical field is created around the patient, and the coils on the instrument are connected to a DC energy source such that there is a constant energy signal emitting from the coils. The coils create a disturbance in the electrical field as they move through the field, and location of the instrument in the 3D coordinate space is calculated by determining the location of the disturbance in the energy field relative to the sensors.

As described above, delivery of a valve percutaneously to a remote access site in the body via the vascular system and delivery of devices for treating cardiac valve disease can be challenging because precise manipulation of the surgical tools is more difficult when the surgeon cannot see the area that is being accessed and when the heart is moving. Thus, there is a need for heart valve placement or repair systems having visualization capabilities that permit the surgeon to quickly, easily and securely implant a heart valve or repair a heart valve in a patient with minimal resulting trauma to the patient. In certain cases, there is a further need for heart valve placement systems that can implant such valves into a failed bioprosthesis, which also requires precise manipulation by a surgeon. In addition, there is a need for heart valve repair systems that can repair a failed or failing heart valve or a failed or failing bioprothesis. Such systems should further provide the surgeon with a high degree of confidence that a valve has been properly positioned within the patient's heart during surgery.

SUMMARY

While a variety of systems and devices have been developed to provide tracking and visualization in certain areas of the body for a number of different applications, these systems are not being used and are not generally adaptable to be used for placement or repair of heart valves in certain locations in the heart. That is, the types of navigation systems used for other areas of the body have different operating parameters and requirements that are different from those needed for percutaneous implantation of a valve or percutaneous repair of a valve within a patient's heart. The present disclosure advantageously addresses these operating parameters and requirements while minimizing the use of fluoroscopy and providing a 3-dimensional view of the heart structure.

In one aspect of the disclosure, a delivery system is provided for percutaneous delivery of a heart valve to a predetermined position in the heart of a patient, where the delivery system itself includes features that allow it to be accurately positioned in the heart. In another aspect of the disclosure, a delivery system is provided for percutaneous repair of a heart valve in the heart of a patient, where the repair system itself includes features that allow it to be accurately positioned in the heart. For example, a delivery or repair system can include multiple ferromagnetic elements spaced from each other along the length of an elongated body. Preoperative and intraoperative imaging can help guide the device or delivery system to the desired position in the heart using an external magnetic field, which drives the ferromagnetic objects on the device or delivery system into position. The imaging, navigation, and movement are all merged.

In another aspect of the disclosure, a method and device are provided that involve imaging the native root using an interoperative technique, then introducing a device that is easily visualized in a chosen imaging modality. The type of balloon used (e.g., flow-through or non-flow-through) will determine whether the cardiac motion will then need to be reduced. The balloon is then inflated and the aortic root is imaged so that the best size can be chosen that does not allow migration or force the leaflets to block the coronaries.

BRIEF DESCRIPTION OF THE DRAWINGS

The present disclosure will be further explained with reference to the appended Figures, wherein like structure is referred to by like numerals throughout the several views, and wherein:

FIG. 15 is a block diagram illustrating one embodiment of the disclosure.

DETAILED DESCRIPTION

Figure 1:
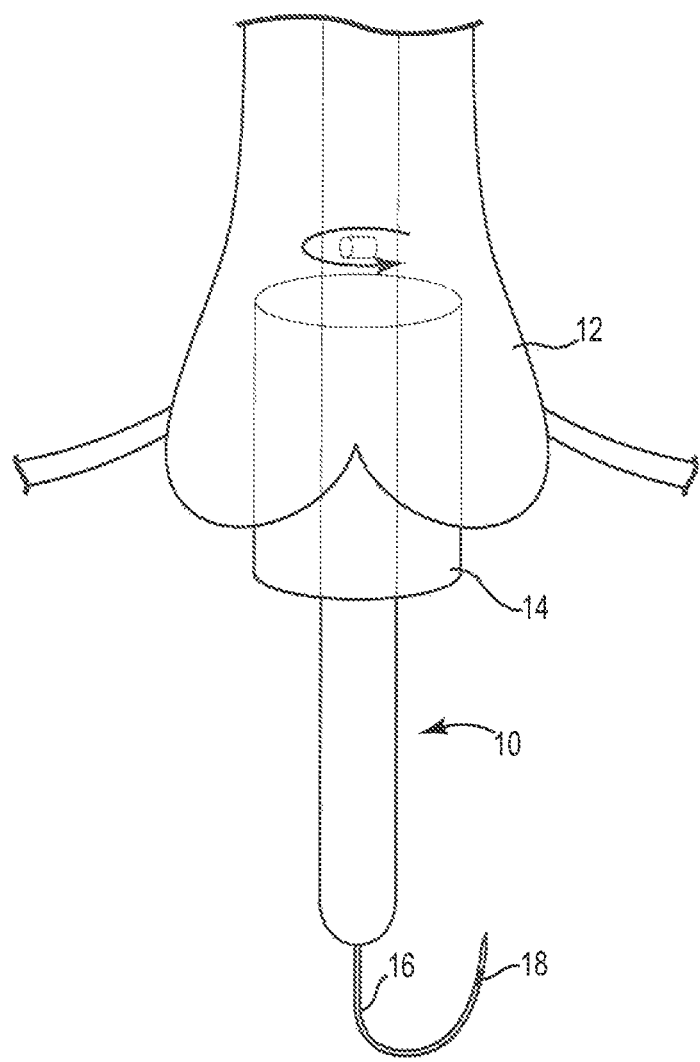
FIG. 1 is a schematic front view of one embodiment of a heart valve delivery system of the disclosure, including at least one ferromagnetic element used for valve placement.

As set out above, the navigation systems of the present disclosure are particularly directed to percutaneous replacement and repair of cardiac valves, which can be performed using a number of different delivery systems. One exemplary delivery system and its use may correspond to that described in the above-cited Tower, et al. applications, where the stented valve can be expanded against a failed native or prosthetic valve. The delivery system can be advanced to the desired valve implant site using a guidewire, after which the sheath is moved proximally, exposing the balloon mounted on an inner catheter. The balloon is expanded, which thereby expands the stented valve until it reaches a desired outer diameter where it contacts the wall of a heart vessel. The balloon is then deflated and the delivery system is withdrawn proximally. In order to locate the valve and delivery systems during the surgical procedure, one or a combination of the methods, devices, and systems of the disclosure described herein may be used.

Notably, although the term "replacement" normally signifies removal of a diseased valve and implantation of a new valve, in accordance with the disclosure, a new valve may also be implanted directly over top of or adjacent to a diseased native valve, which may also generically be referred to as "replacement" or may instead be referred to as "implantation". Both types of procedures are contemplated for use with the present disclosure. In many cases, an implantation procedure can be the same as a replacement procedure without the removal of the diseased valve.

Certain embodiments of the disclosure described herein may only be used for placement of particular valves (e.g., aortic valves); however, some embodiments of the disclosure may be useful for valve placements in more than one area of the heart (e.g., mitral valves, pulmonic valves), with the methods requiring different navigation of the device to these areas of the heart. In any of the methods of the disclosure, it is desirable to avoid placing the valve prosthesis in a position that blocks the coronaries during the surgical process.

The location for valve implantation or repair can be determined by various imaging modalities such as ultrasound imaging, CT, MRI, PET, fluoroscopy, etc. The coordinates for the desired location for valve implantation or repair from any of these imaging modalities can be determined. Two or three-dimensional imaging may be performed as well as phased or annular array imaging may be performed. For example, two or three-dimensional echocardiography, such as transesophageal echocardiography, or ultrasound imaging, such as transthoracic ultrasound imaging may be employed as described in U.S. Patent Application Publication No. 2005/0080469, the disclosure of which is incorporated by reference in its entirety. In one embodiment of the disclosure, an imaging device may be used to illuminate a valve implantation site, a valve repair site and/or surgical site.

In one embodiment of the disclosure, an ultrasound imaging transducer assembly may be used to provide a real-time or multiplexed echo feedback on the progress of the valve implantation or repair. In one embodiment of the disclosure, the changes in mechanical properties of tissue may be observed in eco imaging. In addition, an ultrasound transducer may sense reflections from the targeted tissue such as backscatter echo and spatial compound imaging, etc. to provide one or more properties of the tissue imaged.

In addition, with the methods of the disclosure, it is often desirable to use a sizing balloon prior to valve placement to determine the proper size of the valve that will be implanted. One example of a sizing technique is to use an expandable and retractable sizing device made out of a material such as Nitinol. Such a sizing device can be navigated to the implantation site, such as by using an MRI compatible device, and then an image can be taken of the sizing device in its compressed or retracted condition. The device can then be expanded until it is in contact with the vessel at the implantation site and another image can be taken of the device in its expanded condition. These images of the sizing device in its compressed condition and expanded condition are then compared with each other and with the sizes of the available valves to determine the optimum valve for implantation. Additionally or alternatively, the pressure increase of a sizing device (e.g., an expandable balloon-type device) can be monitored and recorded during its expansion, and the data obtained can be compared to a pre-measured pressure increase of a similar device. That is, the information obtained from the pressure increase in the sizing device will correspond with a certain external size of the device, which in turn will correspond to a valve of a certain size. It is further contemplated that the implantation device can release dye into the implantation area while checking the pressures to determine if the device is blocking any of the coronaries.

In some embodiments of the disclosure, electromagnetic navigation can be performed with 4D ultrasound, as opposed to using fluoroscopy, CT, or MRI, for example. For one particular example, the 4D ultrasound can be used for intraoperative navigation instead of using fluoroscopy in order to obtain better resolution of the heart.

Referring now to the Figures, wherein the components are labeled with like numerals throughout the several Figures, and initially to FIG. 1, a delivery system 10 is illustrated, with a prosthetic valve 14 mounted thereon and being inserted into an aorta 12 of a patient. Delivery system 10 includes a guide wire 16 and at least one sensor 18, e.g., a ferromagnetic element, that establishes an electric field for the system 10 and can be used to give rotation to the valve. Although it is possible that only one ferromagnetic element 18 is provided, multiple ferromagnetic elements may be provided at spaced-apart locations along a portion of the length of the delivery device to provide additional data regarding navigation of the system 10. In any case, intraoperative imaging or preoperative images can be used to define alignment of annuloplasty devices, for example. The use of these ferromagnetic elements can precisely locate points within the heart using an external, 3-dimensional frame of reference.

Each element 18 of a particular delivery system 10 may be the same or different from other ferromagnetic elements 18 in that same system. When the elements are different from each other, the ferromagnetic elements may be distinguishable to provide the navigation process with an additional assurance of accuracy. In particular, each sensor 18 may have a variety of different shapes and forms, such as a coil that is wound around the delivery system with a predetermined number of wrappings, a clamp or collar that extends completely or partially around the delivery system at certain locations, or any other configuration that can be securely attached to the delivery system. Further, the sensor elements 18, e.g., ferromagnetic elements, should be sufficiently large that they are visible using the imaging devices of the system, but should not be so large that they interfere with the valve replacement process.

Figure 2:
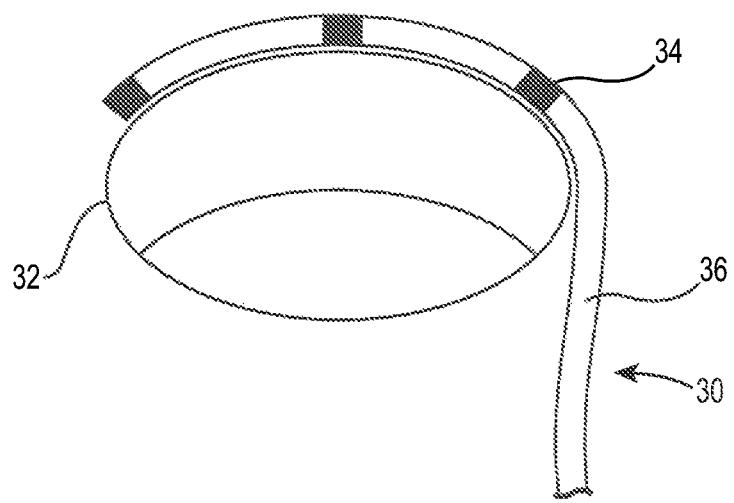
FIG. 2 is a schematic front view of a portion of a delivery system for an annuloplasty device, which is positioned adjacent to a valve annulus.

FIG. 2 is a schematic view of a delivery system 30 positioned relative to an annulus 32 of a patient's heart. Delivery system 30 includes multiple sensors 34, e.g., ferromagnetic elements, spaced from each other along the length of an elongated body 36. The number, size, spacing, and type of sensor elements 34 may be selected to determine certain characteristics of the annulus of the patient. In any case, interoperative imaging or preoperative images can be used to define the alignment of a valve repair device, e.g., an annuloplasty device, that is to be implanted.

The delivery systems of FIGS. 1 and 2 can be used with a system that moves the sensor objects, e.g., ferromagnetic objects, on the devices via an externally generated magnetic field. In one specific example, preoperative and intraoperative imaging can help guide the device or delivery system to an annulus (e.g., a mitral annulus) using a system that involves the use of an external magnetic field which drives ferromagnetic objects placed on a catheter into their desired position. The information provided by the imaging, navigation, and movement are advantageously merged together for use by the physician or surgeon.

Figure 3:
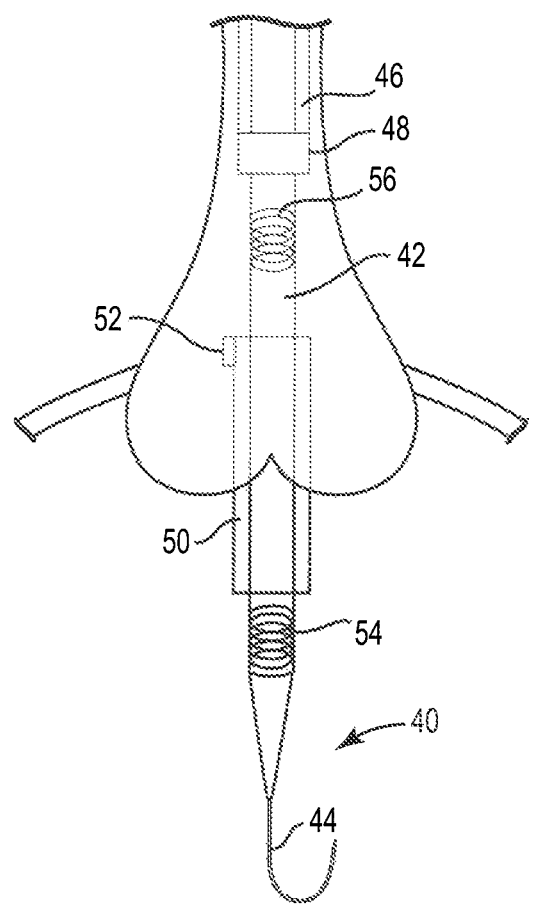
FIG. 3 is a schematic front view of another embodiment of a heart valve delivery system of the disclosure.

FIG. 3 illustrates a delivery system 40, which includes a catheter 42, a guide wire 44, a sheath 46, and one or more sensor markers 48 on the sheath 46. The sensor marker or markers 48 on the sheath 46 allow for precise exposure of the stent or an associated balloon during a stent delivery process. That is, the location of each sensor marker 48 can be detected and therefore can allow for precise movement of the sheath 46. The delivery system 40 further includes a prosthetic valve 50 that has at least one sensor marker 52, e.g., a radiopaque marker, to allow for rotational orientation of the valve 50. This delivery system 40 is used for pre-screening or pre-imaging of the anatomy of a patient to thereby provide a roadmap of the native anatomy. The delivery system 40 can further be used to image with a balloon or sizer that is deployed into the root at various pressures, which will allow for a measurement of compliance. The system also includes a first sensor navigation coil 54 positioned adjacent to one end of the valve 50, and a second sensor navigation coil 56 positioned adjacent to the opposite end of the valve 50.

Figure 4:
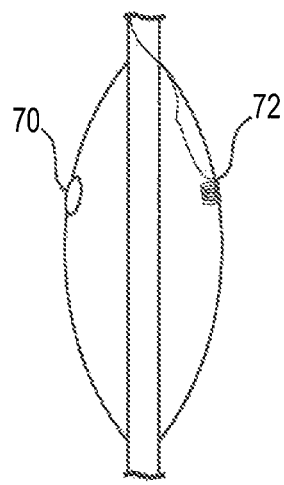
FIG. 4 is a schematic front view of a portion of another embodiment of a heart valve delivery system of the disclosure.

FIG. 4 further illustrates a portion of a delivery system that includes a sensor marker 70 that may be a radiopaque material, gadolinium, dysprosium oxide, or another material that makes it visible in certain imaging modalities. For example, gadolinium (Gd) markers can be used for MRI procedures. The system further includes at least one sensor electromagnetic receiver coil or electrode 72. Sensor marker 70 is positioned on a portion of the system that may be referred to as the passive portion or segment of the system, and the sensor electromagnetic coil or electrode 72 is positioned on a portion of the system that may be referred to as the active portion or segment of the system. This system can be used to capture preoperative images, register the images to the intraoperative patient anatomy, and navigate within the anatomy using electromagnetic or electropotential methods or passively using intraoperative MRI. Each sensor electromagnetic coil or electrode 72 may be placed at a predetermined location on the catheter delivery system and on its associated implantable valve. The predetermined location or locations can be chosen for functional components to ensure proper positioning. For example, a sensor element, e.g., an electromagnetic coil, can be placed at the tip of a catheter so that it is possible to continuously track and visualize the catheter tip in real time without the continuous use of fluoroscopy.

In another alternative, one or more electromagnetic coils can be placed at the end and/or the middle and/or other intermediate location(s) of an inflatable balloon to track the location of the balloon relative to the annulus of the target valve. In this way, the location of the balloon can be determined so that the catheter can be maneuvered to accurately position the balloon at a predetermined location for its inflation and for valve deployment. In a similar manner, one or more sensor electromagnetic coils can additionally or alternatively be placed on a valve in order to enable an operator to track and visualize the valve on the delivery device and to accurately position the valve in a predetermined location. One advantage that is provided by the use of these sensor electromagnetic coils is that the coils provide an operator with the ability to track the devices (e.g., valves) in a different visualization modality into which relatively detailed anatomical information can be incorporated. For example, the tracking or positioning of the sensor electromagnetic coils can be superimposed over a 3-dimensional preoperative image of the patient's anatomy, which provides more detailed information of the cardiac tissue without contrast use and without repeated exposure to x-rays or other radiation.

Figure 5:
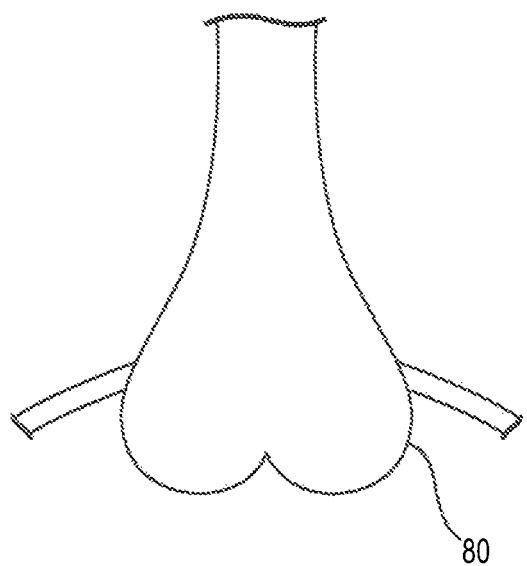
FIGS. 5 and 6 are schematic front views of an aortic root of a heart, with FIG. 6 illustrating a delivery system positioned relative to the aortic root.
Figure 6:
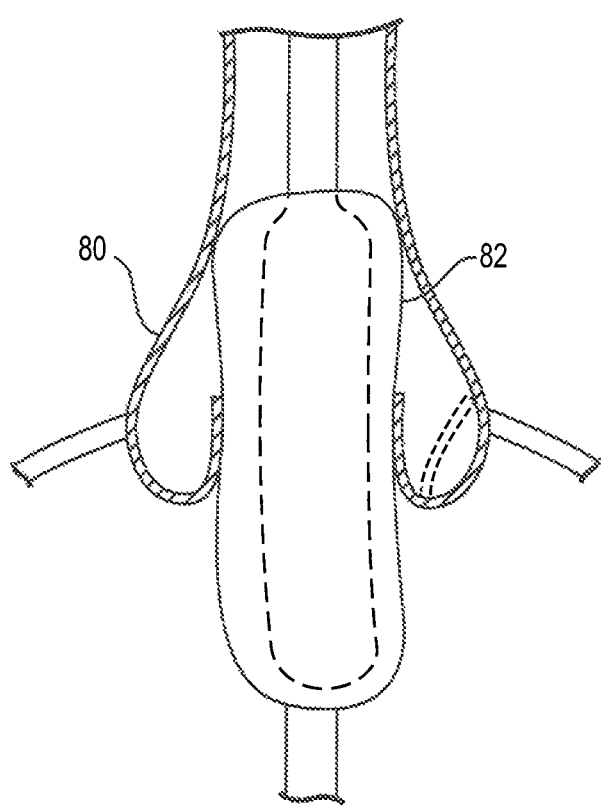

FIGS. 5 and 6 illustrate a method and device for delivering a heart valve in accordance with the disclosure. In general, the native root 80 is initially imaged using an intraoperative technique, such as fluoroscopy, 4D echo, interventional MRI, and the like. This image becomes the baseline or "roadmap" that is used for the remainder of the processes. A balloon 82 or stent may then be deployed or a stent can be used to size the aortic valve at various pressures or stages. The chosen balloon or stent should be easily visualized in the chosen imaging modality (e.g., if interventional MRI is used, iron or gadolinium can be used). That is, the materials chosen for the balloon or stent should make the device conspicuous with the imaging technique that is used.

The blood flow may then optionally be reduced by controlled intermittent asystole, high rate pacing, or other technique(s) used for slowing cardiac motion or stopping the heart for extended periods of time. The balloon 82 or stent may alternatively be designed to allow blood to flow or pass through it, in which case the blood flow would not necessarily need to be reduced. A non-compliant balloon can be inflated to various pressures and/or sizes and the aortic root can be imaged while looking at the leaflet anatomy. The balloon can then be chosen to be the best size that will not migrate but that also does not force the leaflets to block the coronaries. Alternatively or additionally, a compliant balloon, can be used to determine the compliance of the aortic root. If stents are used, they are preferably recapturable and the leaflets preferably function when the device is deployed but not released. In any case, the deployment diameter or force chosen must prevent the valve leaflets from covering the coronary ostia.

In accordance with the disclosure, additional aspects of methods and devices for balloon sizing and valvuloplasty using a valvuloplasty/sizer balloon include a number of steps, some of which are optional. In one embodiment, a valvuloplasty/sizer balloon is selected, where multiple balloons can be provided in a number of different sizes and/or where each balloon can be provided as a single balloon (compliant or non-compliant), or may comprise multiple balloons that are coaxial or placed serially in a linear arrangement on the same catheter. The balloon can include features that allow for at least some blood flow, such as a certain level of porosity and/or at least one central hole, for example. The chosen balloon or balloons can then be inflated to a first pressure that correlates with a known radial force that will typically be required by a certain transcatheter valve stent that will subsequently be implanted.

Once the balloon or balloons are inflated to this first pressure, a number of measurements can be performed, which can be selected for a particular application from a number of measurement options. One such measurement is to measure the diameter or other dimensions of the balloon at various anatomical locations (e.g., annulus, sinotubular junction, ascending aorta, sinus region, and the like) using a balloon silhouette or radiopaque fluid within the balloon. The circularity of diameters at one or more anatomical locations can then be measured. The orifice area can then be calculated. The clearance between the native leaflets and the coronary arteries can then be measured with the balloon or balloons inflated to simulate the dimensions of the transcatheter valve stent when it is deployed. The balloon can optionally include integral markings to facilitate making this measurement. The balloon could also have indicia or other detectable features that indicate particular structural features that allow a clinician to determine a desirable stent height to avoid the coronary ostia, to provide stable seating of the valve in its space, and the like. The balloon catheter can incorporate means (e.g., transducer or calibrated joint or feature) to assess the dislodgement or migration force of the transcatheter valve stent that will be deployed.

Next, the parameters of the system can be evaluated. First, the calcific locations of the native valve can be identified, and a determination can be performed of the mobility of the calcium under balloon inflation. A verification can be made of the coronary clearance and patency with native leaflets pushed out by the balloon, which thereby simulates the transcatheter valve stent. The resulting effect on the adjacent anatomy (e.g., the mitral valve orifice) can also be evaluated, along with the effect on the heart rhythm (e.g., heart block, fibrillation, and the like).

After the chosen measurement and evaluation steps have been completed, these results can be compared against target values or guidelines to determine whether an acceptable result has been achieved. If acceptable results have not been achieved, some or all of the previous steps can be performed at one or more additional pressures that are different than the first pressure, where each new pressure that is used corresponds to a different radial force, until an acceptable result is achieved. When an acceptable result is achieved, then a balloon valvuloplasty can be performed, where the optimum stent radial force, stent height, and stent profile can be selected based on the measurements and evaluation parameters discussed above. However, if an acceptable result cannot be achieved even after using different pressures, it is contemplated that the procedure be abandoned in that the valve is not suitable for implant at this location for at least one reason (e.g., that the coronaries are occluded at all pressures, that the valve will migrate at all pressures, that arrhythmia or heart block will occur at all pressures, that the diameter and/or circularity are outside the feasibility range for the device, and/or the like). It is noted that the measurements may optionally be repeated after the balloon valvuloplasty is performed.

In the methods of imaging of the disclosure, a number of materials can be used as contrast medium for the components of the systems. These materials can provide contrasting markers that are combined for improved imaging results. For one example, when magnetic resonance imaging (MRI) techniques are used, iron can be used for imaging. Alternatively, dysprosium oxide can be characterized as the negative material and be illustrated as a black area on a display screen, and gadolinium can be characterized as the positive material and be illustrated as a white area. For another example, when echocardiographic techniques are used, gas can be shown as a black area on a display screen, and microspheres or nonocoatings may be shown as a white area. For yet another example, when computed tomography (CT) techniques are used, markers can be provided with different materials that are illustrated as either black or white areas, such as can be provided by platinum, tantalum, BaSO$_4$, and the like.

Figure 7:
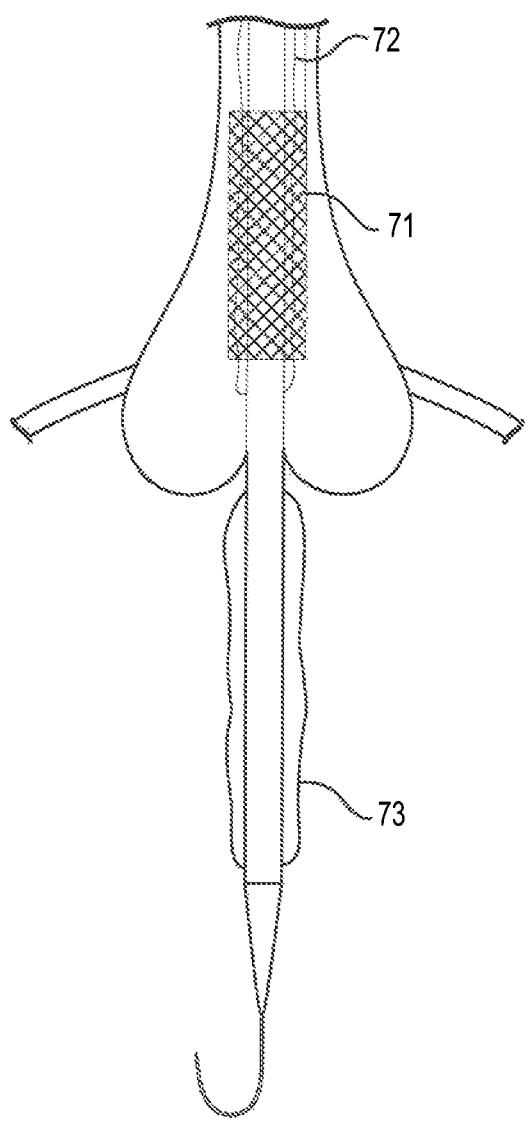
FIG. 7 is a schematic front view of another embodiment of a heart valve delivery system of the disclosure.

FIG. 7 illustrates a system that provides the dual function of deploying a stent 71 with an inflatable and expandable balloon 72, while also providing a dilation balloon or leaflet resection tool 73. The dilation balloon can be used for dilation, measurement, and/or excising of the native valve.

FIG. 15 illustrates a method 150 of determining whether a replacement heart valve is appropriate for implanting in a section of a heart of a patient described with reference to FIGS. 5 and 6. An expandable distal end portion of a sizing device is inserted via catheter into the section of the heart of the patient into which the replacement heart valve is to be implanted at 152. Selective expansion of the distal end portion of the sizing device applies a selected radial force to the section of the heart and simulates at least one property of the replacement heart valve in a deployed state. The section of the heart is imaged while the distal end portion of the sizing device in an expanded state applies a radial force to the section of the heart during heart rhythm at 154. The section of the heart is reimaged while the distal end portion of the sizing device in a contracted state does not apply the radial force to the section of the heart during heart rhythm at 156. Dimensional characteristics of the section of the heart are derived based on images of the distal end portion of the sizing device applying and not applying the radial force to the section of the heart at 158. A determination is made as to whether the replacement heart valve is appropriate for implantation in the section of the heart based on the derived dimensional characteristics of the section of the heart at 160.

Figure 8:
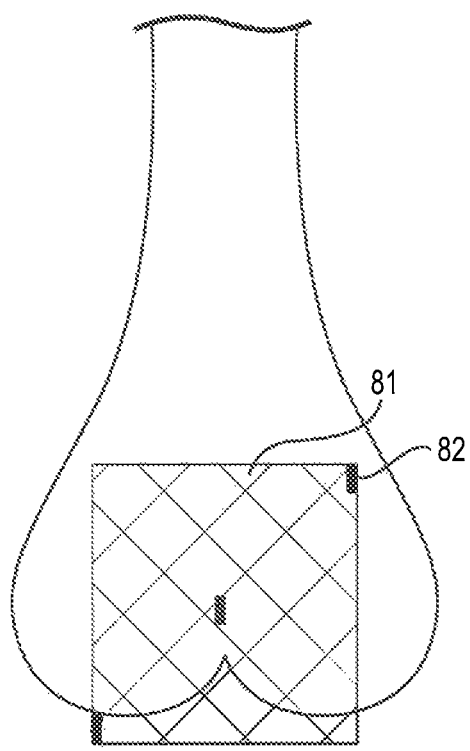
FIG. 8 is a schematic front view of another embodiment of a delivery system of the disclosure.

FIG. 8 shows a stent 81 positioned relative to an aortic valve, where the stent includes multiple sensor markers 82 spaced from each other. These sensor markers provide visualization so that post-operative follow-up can be accomplished more easily. In particular, having specific, easily identifiable markers facilitates being able to repeatably follow the stent over time and to measure deformation of the stent, as well as to track any fractures that may occur relative to the identifiable markers. The markers can also provide guidance for additional valves or stents that may need to be positioned relative to the stent. For one example, a second stent or valve can have the same or similar markers as the original stent or valve so that a physician can align the markers of both valves or stents in order to deploy the new valve in the desired position relative to the old stent or valve. In another example, the second stent or valve can have different markers than the original stent or valve, such that a particular relationship or positioning of the new and old stents or valves can be achieved by positioning the markers in a certain arrangement relative to each other.

Figure 9:
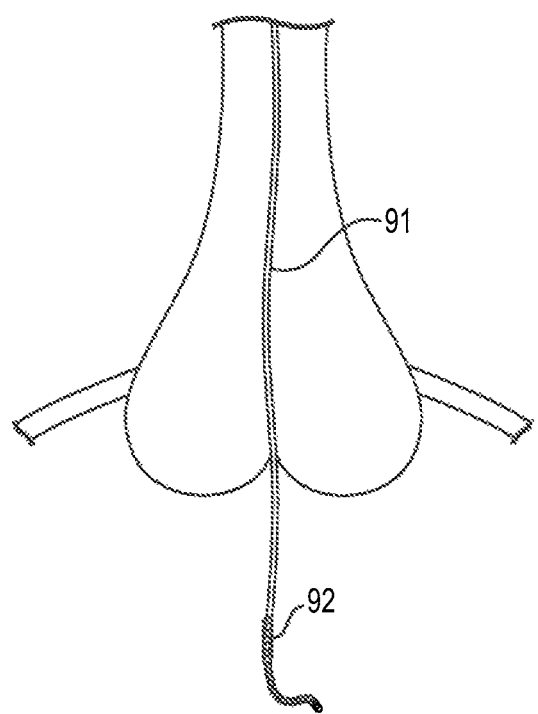
FIG. 9 is a schematic front view of a guide wire of a heart valve delivery system of the disclosure.

FIG. 9 is an illustration of an embodiment of an imaging technique in which a guide wire 91 includes one or more sensors 92, for example, an echogenic coating, a RF receiver coil, a gadolinium marker, an electrode, or the like. This element or portion of the guide wire allows precise passage of the wire through a stenotic aortic valve using an intra-operative imaging mode. Using the techniques described herein to visualize or guide a component or device with these markers, the guidewire can be guided across the stenotic orifice, which can be challenging if it is heavily calcified. This can be accomplished more easily if the guidewire is steerable.

Figure 10:
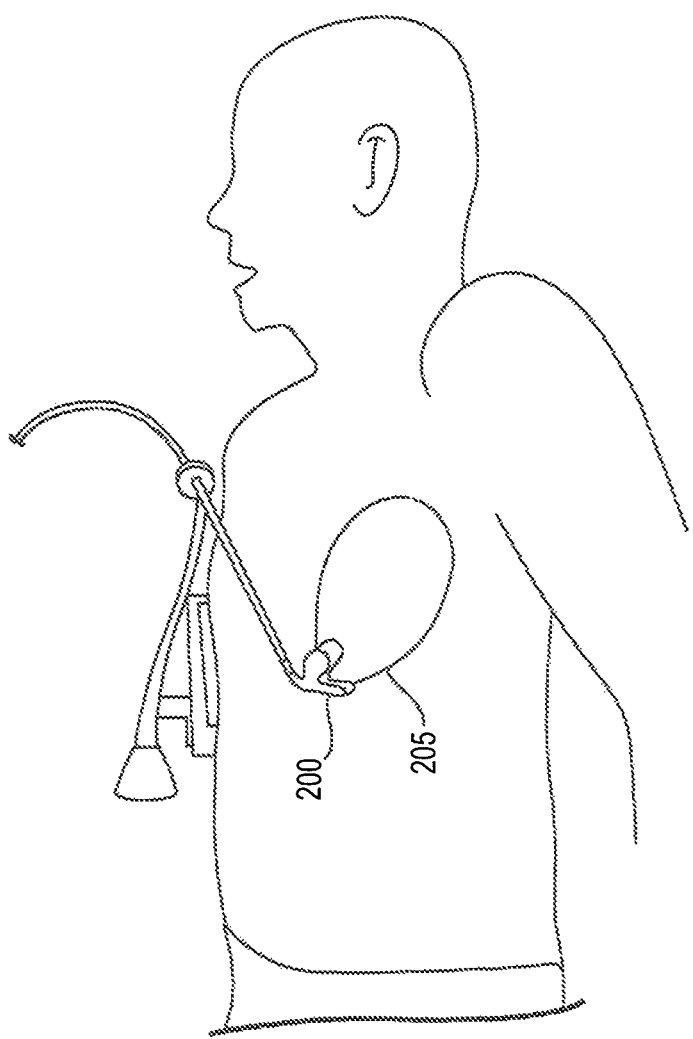
FIG. 10 is an illustration of a tissue-engaging device of the disclosure.

FIG. 10 is an illustration of a tissue-engaging device 200 being used in a closed chest, non-sternotomy procedure to position the heart 205 into a non-physiological orientation. Positioning the heart in a non-physiological orientation can provide access to areas of the heart that normally would not be available to one or more devices, for example, through a thoracotomy or port, through the patient's esophagus or trachea, or positioned outside the chest.

Figure 11:
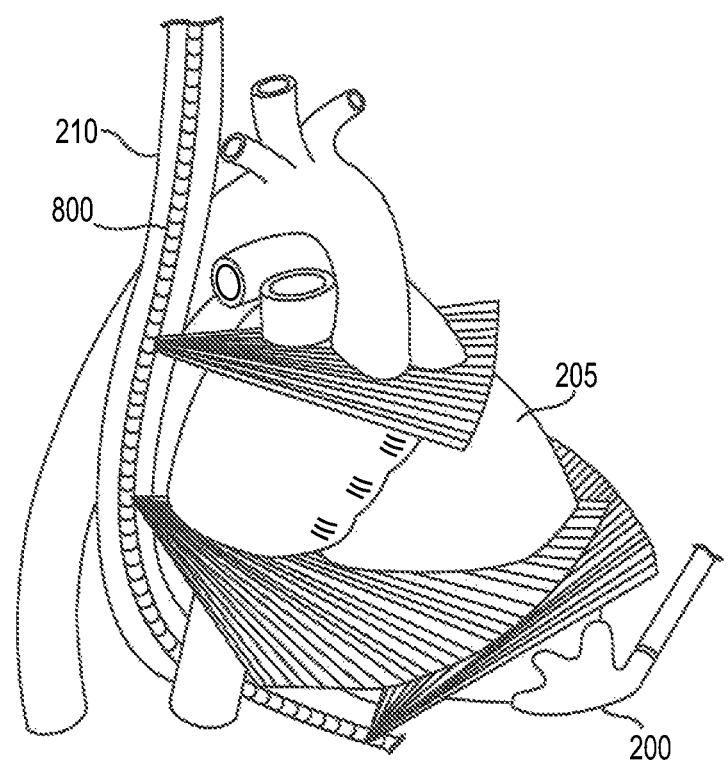
FIG. 11 is an illustration of an imaging device of the disclosure.

In one embodiment of the disclosure, an imaging device 800 may be used to image tissue such as heart tissue as shown in FIG. 11. The imaging device may be appropriately sized to allow its placement within the esophagus of the patient. Alternatively, the imaging device may be appropriately sized to allow its placement within the trachea and/or bronchi of the lungs of the patient. Alternatively, one or more imaging devices may be positioned through one or more other body cavity openings of the patient and/or positioned on the skin of the patient. For example, one or more imaging devices may be positioned through the mouth, the nose, the anus, the urethra and/or the vagina. In one embodiment of the disclosure, one or more imaging devises may be placed through a port, a stab wound, or an incision. In one embodiment of the disclosure, a valve replacement device or a valve repair device may include one or more imaging capabilities. For example, ultrasound imaging capabilities may be incorporated into a valve replacement device or valve repair device so that a single device could be used to both image and repair valve tissue or image and implant a valve bioprosthesis.

In one embodiment of the disclosure, once one or more imaging devices are placed in the desired position, cardiac tissue is then imaged and the location of valve tissue to be treated is determined. To image cardiac tissue not positioned within the focusing range of an imaging device, a tissue-engaging device 200 may be used to move and position the tissue of interest within the focusing range of the imaging device. The tissue-engaging device 200 may be used to position tissue prior to an imaging procedure, during an imaging procedure and/or following an imaging procedure. In addition to cardiac tissue, other tissue types and/or organs may be positioned and imaged by one or more positioning and imaging devices. In one embodiment of the present disclosure, the positioning or tissue-engaging device may comprise one or more imaging capabilities, e.g., ultrasound imaging.

In one embodiment of the disclosure, a tissue-engaging device may include one or more ultrasound imaging elements. The tissue-engaging device comprising one or more ultrasound imaging elements may be used to move and position tissue. A tissue-engaging device may be used to position tissue prior to a valve procedure, during a valve procedure and/or following a valve procedure, for example, a valve implantation or repair procedure. In addition to cardiac tissue, other tissue types and/or organs may be imaged by one or more ultrasound imaging elements of the device. The distal end of the tissue-engaging device may be positioned within a patient through an incision, a stab wound, a port, a sternotomy and/or a thoracotomy. An endoscope may be used to help position the tissue-engaging device.

In one embodiment of the disclosure, an imaging device or system may comprise one or more switches to facilitate its regulation by a physician or surgeon. One example of such a switch is a foot pedal. The switch may also be, for example, a hand switch, or a voice-activated switch comprising voice-recognition technologies. The switch may be incorporated in or on one of the surgeon's instruments or any other location easily and quickly accessed by the surgeon or medical practitioner. In one embodiment, a switch may be physically wired to the imaging device or it may be a remote control switch.

In one embodiment of the disclosure, an imaging device may be based on one or more imaging modalities such as ultrasound imaging, CT, MRI, PET, fluoroscopy, echocardiography, etc. An imaging device may have two and/or three-dimensional imaging capabilities as well as phased and/or annular array imaging capabilities. For example, two or three-dimensional echocardiography, such as transesophageal echocardiography (TEE), or ultrasound imaging, such as transthoracic ultrasound imaging may be possible with use of an imaging device.

The imaging device may comprise one or more light sources and/or illuminating materials, e.g., glow-in-the-dark materials. For example, one or more portions of a tissue-engaging device and/or one or more portions of a valve replacement or repair delivery system may comprise one or more glow-in-the-dark materials. The imaging device may be based on fluorescence technologies. The imaging device may comprise fiber optic technologies; for example a fiber optic conduit may deliver light from a remote light source to an area adjacent a treatment site.

An imaging device may comprise a light pipe, for example, to illuminate the tissue-engaging device and/or a valve replacement or repair delivery device and/or the surgical field adjacent. A transparent, semi-transparent or translucent tissue-engaging head may be illuminated merely by placement of the end of a light pipe or other light source adjacent a portion of the tissue-engaging device. A transparent, semi-transparent or translucent portion of a valve replacement or repair device may be illuminated merely by placement of the end of a light pipe or other light source adjacent a transparent, semi-transparent or translucent portion of a valve replacement or repair delivery device or system.

An imaging device may include a visual display or monitor, such as, for example, a LCD or CRT monitor, to display various amounts and types of information. By software control, the user may choose to display the information in a number of ways. The imaging device may be powered by AC current, DC current, or it may be battery powered either by a disposable or re-chargeable battery. The imaging device may provide UV, IR and/or visible light. The imaging device may include a laser. The imaging device may be incorporated into tissue-engaging device and/or a valve replacement or repair device or system or it may be incorporated into a separate device. A separate imaging device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. A separate imaging device may be positioned through one or more body cavity openings of the patient and/or positioned outside the patient, e.g., near the patient or on the skin of the patient. One or more imaging devices may be positioned in the esophagus, the trachea and/or the bronchi of the lungs.

In one embodiment of the disclosure, the beating of a patient's heart may be controlled before a cardiac valve procedure, during a cardiac valve procedure, or following a cardiac valve procedure, e.g., a valve replacement procedure or a valve repair procedure. In one embodiment of the disclosure, a nerve stimulator device comprising one or more nerve stimulation electrodes may be used to stimulate the patient's vagal nerve to slow or stop the patient's heart during a valve replacement or valve repair procedure. The patient may be given one or more drugs to help stop the beating of the heart and/or to prevent "escape" beats. Following vagal stimulation, the heart may be allowed to return to its usual cardiac rhythm. Alternatively, the heart may be paced, thereby maintaining a normal cardiac output or to increase cardiac output. Vagal stimulation, alone or in combination with electrical pacing and/or drugs, may be used selectively and intermittently to allow a surgeon to perform a valve replacement or valve repair procedure on a temporarily stopped heart. For example, stimulation of the vagus nerve in order to temporarily and intermittently slow or stop the heart is described in U.S. Pat. Nos. 6,006,134, 6,449,507, 6,532,388, 6,735,471, 6,718,208, 6,228,987, 6,266,564, 6,487,446 and U.S. patent application Ser. No. 09/670,370 filed Sep. 26, 2000, Ser. No. 09/669,961 filed Sep. 26, 2000, Ser. No. 09/670,440 filed Sep. 26, 2000. These patents and patent applications are incorporated herein by reference in their entireties.

Electrodes used to stimulate a nerve such as the vagal nerve may be, for example, non-invasive, e.g., clips, or invasive, e.g., needles or probes. The application of an electrical stimulus to the right or left vagal nerve may include, but is not limited to bipolar and/or monopolar techniques. Different electrode positions are accessible through various access openings, for example, in the cervical or thorax regions. Nerve stimulation electrodes may be positioned through a thoracotomy, sternotomy, endoscopically through a percutaneous port, through a stab wound or puncture, through a small incision in the neck or chest, through the internal jugular vein, the esophagus, the trachea, placed on the skin or in combinations thereof. Electrical stimulation may be carried out on the right vagal nerve, the left vagal nerve or to both nerves simultaneously or sequentially. The present disclosure may include various electrodes, catheters and electrode catheters suitable for vagal nerve stimulation to temporarily stop or slow the beating heart alone or in combination with other heart rate inhibiting agents.

Nerve stimulation electrodes may be endotracheal, endoesophageal, intravascular, transcutaneous, intracutaneous, patch-type, balloon-type, cuff-type, basket-type, umbrella-type, tape-type, screw-type, barb-type, metal, wire or suction-type electrodes. Guided or steerable catheter devices comprising electrodes may be used alone or in combination with the nerve stimulation electrodes. For example, a catheter comprising one or more wire, metal strips or metal foil electrodes or electrode arrays may be inserted into the internal jugular vein to make electrical contact with the wall of the internal jugular vein, and thus stimulate the vagal nerve adjacent to the internal jugular vein. Access to the internal jugular vein may be via, for example, the right atrium, the right atrial appendage, the inferior vena cava or the superior vena cava. The catheter may comprise, for example, a balloon, which may be inflated with air or liquid to press the electrodes firmly against the vessel wall. Similar techniques may be performed by insertion of a catheter-type device into the trachea or esophagus. Additionally, tracheal devices, e.g., tracheal tubes, tracheal imaging devices, and/or esophageal devices, e.g., esophageal tubes, esophageal imaging devices, comprising electrodes may be used.

Nerve stimulation electrodes may be oriented in any fashion along a catheter device, including longitudinally or transversely. Various imaging techniques or modalities, as discussed earlier, such as ultrasound, fluoroscopy and echocardiography may be used to facilitate positioning of the electrodes. If desired or necessary, avoidance of obstruction of air flow or blood flow may be achieved with notched catheter designs or with catheters, which incorporate one or more tunnels or passageways.

In one embodiment of the disclosure, the location of the electrodes is chosen to elicit maximum bradycardia effectiveness while minimizing current spread to adjacent tissues and vessels and to prevent the induction of post stimulation tachycardia. Furthermore, a non-conductive material such as plastic may be employed to sufficiently enclose the electrodes of all the configurations to shield them from the surrounding tissues and vessels, while exposing their confronting edges and surfaces for positive contact with the vagal nerve or selected tissues.

Figure 12:
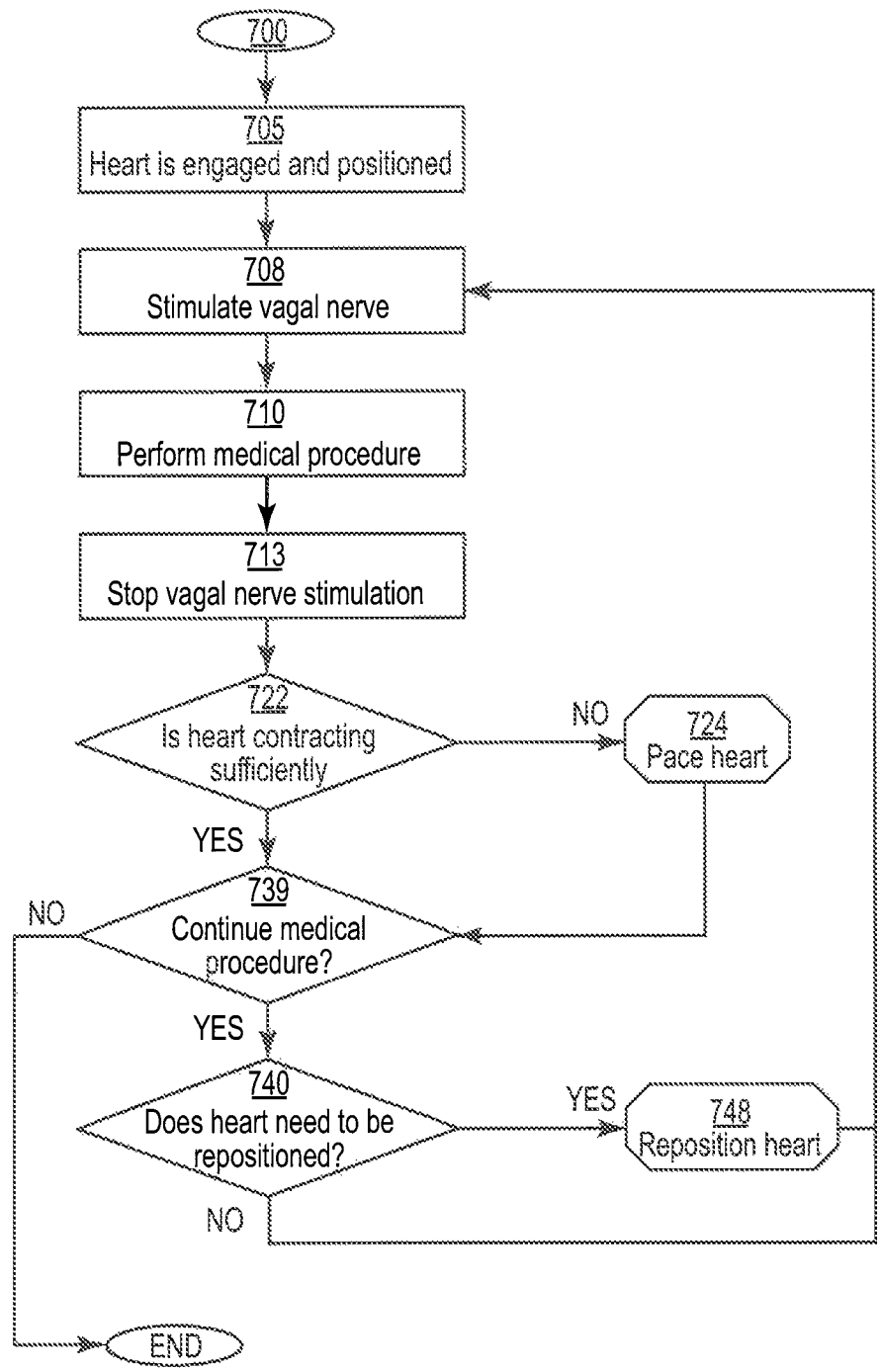
FIG. 12 is a flow diagram of one embodiment of the disclosure.

FIG. 12 shows a flow diagram of one embodiment of the present disclosure. The patient is prepared for a medical procedure at 700. Once the patient is prepared, the heart is engaged and positioned using tissue-engaging device 200 (Block 705). Once the heart is positioned in a desired orientation, e.g., a non-physiological orientation, a nerve that controls the beating of the heart is stimulated to slow down or stop the contractions of the heart (Block 708). Such a nerve may be for example a vagal nerve. During this time, one or more of a variety of pharmacological agents or drugs may be delivered to the patient. Drugs may be administered without nerve stimulation. The types of drugs administered may produce reversible asystole of a heart while maintaining the ability of the heart to be electrically paced. Other drugs may be administered for a variety of functions and purposes. Drugs may be administered at the beginning of the procedure, intermittently during the procedure, continuously during the procedure or following the procedure. Examples of one or more drugs that may be administered include a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine.

Typically, vagal-nerve stimulation prevents the heart from contracting. This non-contraction must then be followed by periods without vagal nerve stimulation during which the heart is allowed to contract, and blood flow is restored throughout the body. Following initial slowing or stopping of the heart, a medical procedure, such as imaging and/or valve replacement or valve repair, is begun (Block 710). In one embodiment of the disclosure, one or more imaging devices may be positioned, e.g., outside a patient or within a patient, for example, within the trachea, bronchi of the lungs and/or esophagus of the patient, and an imaging modality is emitted, for example, ultrasound energy is emitted, from the one or more imaging devices and imaging energy is focused within tissue, e.g., cardiac tissue such as cardiac valve tissue. Following a brief interval of nerve stimulation while the valve replacement or valve repair procedure is performed, nerve stimulation is ceased (Block 713) and the heart is allowed to contract.

In one embodiment of the disclosure, the heart may be free to beat on its own or a cardiac stimulator device or pacemaker comprising one or more cardiac stimulation electrodes may be used to cause the heart to contract (Blocks 722 and 724). Cardiac stimulation electrodes used to stimulate the heart may be, for example, non-invasive, e.g., clips, or invasive, e.g., needles or probes. Cardiac electrodes may be positioned through a thoracotomy, sternotomy, endoscopically through a percutaneous port, through a stab wound or puncture, through a small incision in the chest, placed on the chest or in combinations thereof. The present disclosure may also use various electrodes, catheters and electrode catheters suitable for pacing the heart, e.g., epicardial, patch-type, intravascular, balloon-type, basket-type, umbrella-type, tape-type electrodes, suction-type, pacing electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes. Guided or steerable catheter devices comprising electrodes may be used alone or in combination with the electrodes. In one embodiment of the disclosure, one or more cardiac electrodes, e.g., stimulation and/or monitoring electrodes, may be positioned on a tissue-engaging device. In one embodiment of the disclosure, a cardiac stimulator device may be used to stimulate the heart to beat rapidly to the point cardiac output is minimized or significantly decreased from a normal cardiac output. A valve replacement procedure or valve repair procedure may be performed during rapid pacing of the heart. In one embodiment of the disclosure, the heart may be stimulated to beat so fast it quivers and cardiac output essentially falls to zero during which a valve replacement procedure or valve repair procedure may be performed.

If the valve replacement or valve repair procedure needs to continue or a new valve replacement or repair procedure is to be performed, the heart again may be slowed or stopped via vagal nerve stimulation. In addition, the heart may be repositioned if necessary or desired at Block 748.

In one embodiment of the present disclosure, a probe device sized and shaped to fit within the trachea, bronchi and/or esophagus of the patient may comprise one or more nerve stimulation electrodes, members or elements and one or more ultrasound members or elements. The probe device may be positioned within the trachea, bronchi and/or esophagus of the patient. The nerve stimulation electrodes may be used to stimulate one or more nerves of the patient, e.g., a vagal nerve, as disclosed earlier, while the probe device is positioned within the trachea, bronchi and/or esophagus of the patient. A valve replacement or valve repair delivery system may be used, as disclosed earlier, while the probe device is positioned within the trachea, bronchi and/or esophagus of the patient. The nerve stimulation electrodes may be coupled to a nerve stimulator, e.g., used to stimulate the patient's vagal nerve to slow or stop the patient's heart during a valve replacement or valve repair procedure.

In one embodiment of the disclosure, a valve replacement or valve repair device or system may include a display and/or other means of indicating the status of various components of the device to the surgeon such as a numerical display, gauges, a monitor display or audio feedback. The valve replacement or valve repair device or system may also include one or more visual and/or audible signals used to prepare a surgeon for the start or stop of the valve replacement or valve repair procedure. A controller may synchronize deliver of a bioprosthetic valve between heart beats to reduce inadvertent tissue damage. A controller may be slaved to a nerve stimulator and/or a cardiac stimulator.

Alternatively, a nerve stimulator and/or cardiac stimulator may be slaved to a controller. Alternatively, a controller may be capable of nerve stimulation and/or cardiac stimulation.

In one embodiment of the disclosure, electrodes may be used for cardiac pacing, defibrillation, cardioversion, sensing, stimulation, and/or mapping prior to, during, or following a valve replacement and/or valve repair procedure or procedures.

In one embodiment of the disclosure, a tissue-engaging device and/or a valve replacement or valve repair system or device may be attached to a flexible or rigid hose or tubing for supplying suction and/or fluids from a suitable suction source and/or fluid source to the target tissue surface through one or more suction and/or fluid elements, openings, orifices, and/or ports of the devices and/or systems. The hose or tubing may comprise one or more stopcocks and/or connectors such as luer connectors. Suction may be provided by the standard suction available in the operating room. Suction source may be coupled with a buffer flask and/or filter. Suction may be provided at a negative pressure of between 200-600 mm Hg with 400 mm Hg preferred. As used herein, the terms "vacuum" or "suction" refer to negative pressure relative to atmospheric or environmental air pressure.

Suction may be provided via one or more manual or electric pumps, syringes, suction or squeeze bulbs or other suction or vacuum producing means, devices or systems. Suction source may comprise one or more vacuum regulators, resistors, stopcocks, connectors, valves, e.g., vacuum releasing valves, filters, conduits, lines, tubes and/or hoses. The conduits, lines, tubes, or hoses may be flexible or rigid. For example, a flexible suction line may be used to communicate suction to a tissue-engaging device and/or a valve replacement or valve repair system or device, thereby allowing the systems or devices to be easily manipulated by a physician or surgeon. Another method that would allow the physician or surgeon to easily manipulate the system or device includes incorporation of suction source into tissue-engaging device and/or a valve replacement or valve repair system. For example, a small battery operated vacuum pump or squeeze bulb may be incorporated.

In one embodiment of the disclosure, a suction source may be slaved to a tissue-engaging device, a fluid source, one or more sensors, an imaging device, a drug delivery device, a guidance device and/or a stimulation device. For example, a suction source may be designed to automatically stop suction when a controller sends a signal to stop suction. In one embodiment of the disclosure, a suction source may include a visual and/or audible signal used to alert a surgeon to any change in suction. For example, a beeping tone or flashing light may be used to alert the surgeon when suction is present. A suction source may be slaved to a robotic system or a robotic system may be slaved to a suction source. Suction may be used to secure, anchor or fix a tissue-engaging device and/or a valve replacement or valve repair system or device to an area of tissue. The area of tissue may comprise a beating heart or a stopped heart. Suction may be used to remove or aspirate fluids from the target tissue site. Fluids removed may include, for example, blood, saline, Ringer's solution, ionic fluids, contrast fluids, irrigating fluids and energy-conducting fluids. Steam, vapor, smoke, gases and chemicals may also be removed via suction.

In one embodiment of the disclosure, one or more fluid sources is provided for providing one or more fluids, for example, to a tissue-engaging device, a valve replacement delivery system or device, a valve repair delivery system or device, and/or the patient. A tissue-engaging device may be attached to a flexible or rigid hose or tubing for supplying fluids from fluid source to the target tissue through fluid elements, openings, orifices, or ports of device. A valve replacement or valve repair delivery system or device may be attached to a flexible or rigid hose or tubing for receiving fluids from fluid source and for supplying fluids, if desired, to the target tissue through fluid elements, openings, orifices, or ports of the system or device.

A fluid source of the present disclosure may be any suitable source of fluid. The fluid source may include a manual or electric pump, an infusion pump, a peristaltic pump, a roller pump, a centrifugal pump, a syringe pump, a syringe, or squeeze bulb or other fluid moving means, device or system. For example, a pump may be connected to a shared power source or it may have its own source of power. A fluid source may be powered by AC current, DC current, or it may be battery powered either by a disposable or re-chargeable battery. A fluid source may comprise one or more fluid regulators, e.g., to control flow rate, valves, fluid reservoirs, resistors, filters, conduits, lines, tubes and/or hoses. The conduits, lines, tubes, or hoses may be flexible or rigid. For example, a flexible line may be connected to one or more devices, for example, a tissue-engaging device, an imaging device, a valve replacement device, or a valve repair device to deliver fluid and/or remove fluid, thereby allowing the device or system comprising a fluid source to be easily manipulated by a surgeon. Fluid reservoirs may include an IV bag or bottle, for example.

In one embodiment of the disclosure, one or more fluid sources may be incorporated into a tissue-engaging device and/or a valve replacement device and/or a valve repair device, thereby delivering fluid or removing fluid at the target tissue site. The fluid source may be slaved to a tissue-engaging device and/or a valve replacement device and/or a valve repair device, and/or a suction source, and/or a sensor and/or an imaging device. For example, the fluid source may be designed to automatically stop or start the delivery of fluid while a tissue-engaging device is engaged with tissue or while a valve replacement delivery device is delivering and positioning a valve or while a valve repair device is repairing a valve.

In one embodiment of the disclosure, one or more valve replacement delivery systems, valve repair systems, tissue-engaging devices, suction sources, fluid sources, sensors and/or imaging devices may be slaved to a robotic system or a robotic system may be slaved to one or more valve replacement delivery systems, valve repair systems, tissue-engaging devices, suction sources, fluid sources, sensors and/or imaging devices.

In one embodiment of the disclosure, the fluid source may comprise one or more switches, e.g., a surgeon-controlled switch. One or more switches may be incorporated in or on a fluid source or any other location easily and quickly accessed by the surgeon for regulation of fluid delivery by the surgeon. A switch may comprise, for example, a hand switch, a foot switch, or a voice-activated switch comprising voice-recognition technologies. A switch may be physically wired to a fluid source or it may be a remote control switch. The fluid source and/or system may include a visual and/or audible signal used to alert a surgeon to any change in the delivery of fluid. For example, a beeping tone or flashing light may be used to alert the surgeon that a change has occurred in the delivery of fluid.

In one embodiment of the disclosure, fluids delivered to a tissue-engaging device and/or a valve replacement device and/or a valve repair device and/or an imaging device and/or a sensor may include saline, e.g., normal, hypotonic or hypertonic saline, Ringer's solution, ionic, contrast, blood, and/or energy-conducting liquids. An ionic fluid may electrically couple an electrode to tissue thereby lowering the impedance at the target tissue site. An ionic irrigating fluid may create a larger effective electrode surface. An irrigating fluid may cool the surface of tissue. A hypotonic irrigating fluid may be used to electrically insulate a region of tissue. Fluids delivered according to one embodiment of the disclosure may include gases, adhesive agents and/or release agents.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered with or without a fluid to the patient. Biological agents may be found in nature (naturally occurring) or may be chemically synthesized. Cells and cell components, e.g., mammalian and/or bacterial cells, may be delivered to the patient. A platelet gel or tissue adhesive may be delivered to the patient.

One or more of a variety of pharmacological agents, biological agents and/or drugs may be delivered or administered to a patient, for a variety of functions and purposes as described below, prior to a medical procedure, intermittently during a medical procedure, continuously during a medical procedure and/or following a medical procedure. For example, one or more of a variety of pharmacological agents, biological agents and/or drugs, as discussed above and below, may be delivered before, with or after the delivery of a fluid.

Drugs, drug formulations or compositions suitable for administration to a patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present disclosure, a drug delivery device may be used or incorporated into another device of the present disclosure. The drug delivery device may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the iontophoresis electrodes may also be used as, nerve stimulation electrodes or as cardiac stimulation electrodes.

A drug delivery device may be incorporated into a tissue-engaging device and/or a valve replacement device and/or a valve repair device and/or an imaging device, thereby delivering drugs at or adjacent the target tissue site or the drug delivery device may be placed or used at a location differing from the location of the target tissue site such as a cardiac valve site. In one embodiment of the disclosure, a drug delivery device may be placed in contact with the inside surface or the outside surface of a patient's heart.

In one embodiment of the disclosure, a drug delivery device may be slaved to a tissue-engaging device, a suction source, a fluid source, a sensor, an imaging device, a valve replacement device and/or a valve repair device. For example, a drug delivery device may be designed to automatically stop or start the delivery of drugs during tissue engagement of a tissue-engaging device, during valve replacement via a valve replacement device and/or a valve repair device. The drug delivery device may be slaved to a robotic system or a robotic system may be slaved to the drug delivery device.

The drug delivery device may comprise one or more switches, e.g., a surgeon-controlled switch. One or more switches may be incorporated in or on the drug delivery device or any other location easily and quickly accessed by the surgeon for regulation of drug delivery by the surgeon. A switch may be, for example, a hand switch, a foot switch, or a voice-activated switch comprising voice-recognition technologies. A switch may be physically wired to the drug delivery device or it may be a remote control switch. The drug delivery device may include a visual and/or audible signal used to alert a surgeon to any change in the medical procedure, e.g., in the delivery of drugs. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to one embodiment of this disclosure may include any naturally occurring or chemically synthesized (synthetic analogues) beta-adrenergic receptor blocking agents. Beta-adrenergic receptor blocking agents or .beta.-adrenergic blocking agents are also known as beta-blockers or .beta.-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this disclosure may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to one embodiment of this disclosure may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this disclosure may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to one embodiment of this disclosure may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to one embodiment of this disclosure may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this disclosure may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this disclosure.

Beta-adrenergic stimulation or administration of calcium solutions may be used to reverse the effects of a calcium channel blocker such as verapamil. Agents that promote heart rate and/or contraction may be used in the present disclosure. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

The drug delivery device may include a vasodilative delivery component and/or a vasoconstrictive delivery component. Both delivery components may be any suitable means for delivering vasodilative and/or vasoconstrictive drugs to a site of a medical procedure. For example, the drug delivery device may be a system for delivering a vasodilative spray and/or a vasoconstrictive spray. The drug delivery device may be a system for delivering a vasodilative cream and/or a vasoconstrictive cream. The drug delivery device may be a system for delivering any vasodilative formulation such as an ointment or medicament etc. and/or any vasoconstrictive formulation such as an ointment or medicament etc. or any combination thereof.

The drug delivery device may comprise a catheter, such as a drug delivery catheter or a guide catheter, for delivering a vasodilative substance followed by a vasoconstrictive substance. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. In one embodiment, one catheter may be used to deliver both a vasodilative component and a vasoconstrictive component. The drug delivery device may be a patch, such as a transepicardial patch that slowly releases drugs directly into the myocardium, a cannula, a pump and/or a hypodermic needle and syringe assembly. The drug delivery device may be an iontophoretic drug delivery device placed on the heart.

A vasodilative component may comprise one or more vasodilative drugs in any suitable formulation or combination. Examples of vasodilative drugs include, but are not limited to, a vasodilator, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine and a dopamine D1-like receptor agonist, stimulant or activator. The vasodilative component may include a pharmaceutically acceptable carrier or solution in an appropriate dosage.

A vasoconstrictive component may comprise one or more suitable vasoconstrictive drugs in any suitable formulation or combination. Examples of vasoconstrictive drugs include, but are not limited to, a vasoconstrictor, a sympathomimetic, methoxamine hydrochloride, epinephrine, midodrine hydrochloride, desglymidodrine, and an alpha-receptor agonist, stimulant or activator. The vasoconstrictive component may include a pharmaceutically acceptable carrier or solution in an appropriate dosage.

In one embodiment of the disclosure one or more sensors may be used to sense information regarding the patient or the procedure. A controller may store and/or process such information before, during and/or after a medical procedure, e.g., a valve replacement procedure and/or a valve repair procedure.

A controller may be used according to one embodiment of the present disclosure to control, for example, the energy supplied to one or more energy transfer elements, e.g., electrodes or transducers, of a tissue-engaging device, an imaging device, a valve replacement device and/or a valve repair device. The controller may also gather and process information from one or more sensors. The gathered information may be used to adjust energy levels and times. The controller may incorporate one or more switches to facilitate regulation of the various system components by the surgeon. One example of such a switch is a foot pedal. A switch may also be, for example, a hand switch, or a voice-activated switch comprising voice-recognition technologies. A switch may be physically wired to the controller or it may be a remote control switch. A switch may be incorporated in or on one of the surgeon's instruments, such as surgical site retractor, e.g., a sternal or rib retractor, a tissue-engaging device, a valve replacement device and/or valve repair device, or any other location easily and quickly accessed by the surgeon. The controller may include a display. The controller may also include other means of indicating the status of various components to the surgeon such as a numerical display, gauges, a monitor display or audio feedback.

The controller may incorporate a cardiac stimulator and/or cardiac monitor. For example, electrodes used to stimulate or monitor the heart may be incorporated into a tissue-engaging device, a valve replacement device, a valve repair device and/or an imaging device. The controller may incorporate a nerve stimulator and/or nerve monitor. For example, electrodes used to stimulate or monitor one or more nerves, e.g., a vagal nerve, may be incorporated into a tissue-engaging device, a valve replacement device, a valve repair device and/or an imaging device. The controller may comprise a surgeon-controlled switch for cardiac stimulation and/or monitoring, as discussed earlier. The controller may comprise a surgeon-controlled switch for nerve stimulation and/or monitoring, as discussed earlier. Cardiac stimulation may comprise cardiac pacing and/or cardiac defibrillation. The Controller, tissue-engaging device, a valve replacement device, a valve repair device and/or an imaging device may incorporate a cardiac mapping device for mapping the electrical signals of the heart.

A visual and/or audible signal used to alert a surgeon to the completion or resumption of energy delivery, suction, sensing, monitoring, stimulation and/or delivery of fluids, drugs and/or cells may be incorporated into a controller of the present disclosure. For example, a beeping tone or flashing light that increases in frequency as the energy delivered increases.

In one embodiment of the disclosure, a tissue-engaging device, a valve replacement device, a valve repair device and/or an imaging device may include one or more sensors. Sensor may be incorporated into a tissue-engaging device, a valve replacement device, a valve repair device and/or an imaging device or it may be incorporated into another separate device. A separate sensor device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof.

In one embodiment of the disclosure, a sensor may comprise one or more switches, e.g., a surgeon-controlled switch. One or more switches may be incorporated in or on a sensor device or any other location easily and quickly accessed by the surgeon for regulation of a sensor by a physician or a surgeon. A switch may be, for example, a hand switch, a foot switch, or a voice-activated switch comprising voice-recognition technologies. A switch may be physically wired to the sensor or it may be a remote control switch.

In one embodiment of the disclosure, a sensor may include a visual and/or audible signal used to alert a surgeon to any change in the measured parameter, for example, tissue temperature, cardiac hemodynamics or ischemia. A beeping tone or flashing light may be used to alert the surgeon that a change has occurred in the parameter sensed.

In one embodiment of the disclosure, a sensor may comprise one or more temperature-sensitive elements, such as a thermocouple, to allow a surgeon to monitor temperature changes of a patient's tissue. Alternatively, the sensor may sense and/or monitor voltage, amperage, wattage and/or impedance. For example, an ECG sensor may allow a surgeon to monitor the hemodynamics of a patient during a valve replacement or valve repair procedure. The heart may become hemodynamically compromised during positioning and while in a non-physiological position. Alternatively, the sensor may be any suitable blood gas sensor for measuring the concentration or saturation of a gas in the blood or tissues. For example, the sensor may be a sensor for measuring the concentration or saturation of oxygen or carbon dioxide in the blood or tissues. Alternatively, the sensor may be any suitable sensor for measuring blood pressure or flow, for example a Doppler ultrasound sensor system, or a sensor for measuring hematocrit (HCT) levels.

Alternatively, the sensor may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

In one embodiment of the disclosure, the sensor may be based on potentiometric technology or fiber optic technology. For example, the sensor may comprise a potentiometric or fiber optic transducer. An optical sensor may be based on either an absorbance or fluorescence measurement and may include an UV, a visible or an IR light source.

A sensor may be used to detect naturally detectable properties representative of one or more characteristics, e.g., chemical, physical, mechanical, thermal, electrical or physiological, of a valve replacement system, a valve repair system, and/or a patient's bodily tissues or fluids. For example, naturally detectable properties of patient's bodily tissues or fluids may include pH, fluid flow, electrical current, impedance, temperature, pressure, tension, components of metabolic processes, chemical concentrations, for example, the absence or presence of specific peptides, proteins, enzymes, gases, ions, etc. Naturally detectable properties may include, for example, pressure, tension, stretch, fluid flow, electrical, mechanical, chemical and/or thermal. For example, a sensor may be used to sense, monitor and/or control suction or vacuum delivered from a suction source. A sensor may be used to measure suction between a device and tissue. A sensor may be used to sense, monitor and/or control fluid delivered from a fluid source. A sensor may be used to sense, monitor and/or control energy delivered from a power supply via a controller.

In one embodiment of the disclosure, a sensor may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, vibration sensors, sound wave sensors; magnetic sensors; UV light sensors; visible light sensors; IR light sensors; radiation sensors; flow sensors; temperature sensors; or any other appropriate or suitable sensor.

In one embodiment of the disclosure, one or more sensors may be incorporated into a tissue-engaging device, a valve replacement device, a valve repair device and/or an imaging device or one or more sensors may be placed or used at a location differing from the location of a tissue-engaging device, a valve replacement device, a valve repair device and/or an imaging device. For example, a sensor may be placed in contact with the inside surface or outside surface of a patient's heart during a valve replacement procedure or valve repair procedure.

In one embodiment of the disclosure, a tissue-engaging device, a valve replacement device, a valve repair device, an imaging device, a suction source, a fluid source, a drug delivery device and/or a controller or processor may be slaved to one or more sensors. For example, a tissue-engaging device may be designed to automatically adjust suction if a sensor measures a predetermined sensor value, e.g., a particular suction value.

In one embodiment of the disclosure, the sensor may include a visual and/or audible signal used to alert a surgeon to any change in the one or more characteristics the sensor is sensing and/or monitoring. For example, a beeping tone or flashing light that increases in frequency as tissue temperature rises may be used to alert the surgeon.

In one embodiment of the disclosure, one or more devices may be coupled to a controller, which may include one or more processors. For example, a processor may receive and preferably interpret a signal from one or more sensors. A processor may comprise software and/or hardware. A processor may comprise fuzzy logic. A suitable amplifier may amplify signals from one or more sensors before reaching a processor. The amplifier may be incorporated into a processor. Alternatively the amplifier may be incorporated into a sensor, a tissue-engaging device, a valve replacement device, a valve repair device, a suction source, a fluid source, a drug delivery device, and/or an imaging device. Alternatively, the amplifier may be a separate device. A processor may be a device separate from a sensor, a tissue-engaging device, a valve replacement device, a valve repair device, a suction source, a fluid source, a drug delivery device, and/or an imaging device. A processor may be incorporated into a sensor, a tissue-engaging device, a valve replacement device, a valve repair device, a suction source, a fluid source, a drug delivery device, and/or an imaging device. A processor may control the energy delivered from a power supply. For example, a signal of a first intensity from a sensor may indicate that the energy level from a power supply should be lowered; a signal of a different intensity may indicate that the power supply should be turned off. For example, a processor may be configured so that it may automatically raise or lower the suction delivered to a device comprising suction, the fluids delivered to a device comprising fluid delivery, the drugs delivered to a device comprising drug delivery, energy delivered to a device comprising energy delivery, e.g., from a power supply. Alternatively, for example, the control of the suction source, the fluid source, drug delivery source, the power supply based on output from a processor may be manual.

In one embodiment of the disclosure, a controller may include a visual display or monitor, such as, for example, a LCD or CRT monitor, to display various amounts and types of information. By software control, the user may choose to display the information in a number of ways. The monitor may show, for example, a currently sensed parameter, e.g., blood flow or blood-pressure or cardiac contractions. The monitor may also lock and display the maximum sensed value achieved. Sensed information may be displayed to the user in any suitable manner, such as for example, displaying a virtual representation of valve replacement device, a valve repair device, an imaging device and/or tissue-engaging device on the monitor. Alternatively, a monitor may display the voltage corresponding to the signal emitted from a sensor. This signal may correspond in turn to the intensity of a sensed parameter at the target tissue site. Therefore a voltage level of 2 would indicate that the tissue was, for example, hotter than when the voltage level was 1. In this example, a user would monitor the voltage level and, if it exceeded a certain value, would, for example, turn off or adjust the power supply.

The display of a controller according to one embodiment of the disclosure may be located on a valve replacement device, a valve repair device, a power supply, a tissue-engaging device, a suction source, a fluid source, a sensor and/or an imaging device. An indicator, such as an LED light, may be permanently or removeably incorporated into a valve replacement device, a valve repair device, a power supply, a tissue-engaging device, a suction source, a fluid source, a sensor and/or an imaging device. The indicator may receive a signal from a sensor indicating that a measured parameter has reached an appropriate value. In response, the indicator may turn on, change color, grow brighter or change in any suitable manner to indicate that the particular procedure should be modified or halted. The indicator may also be located on a valve replacement device, a valve repair device, a power supply, a tissue-engaging device, a suction source, a fluid source, a sensor and/or an imaging device and/or may be located on another location visible to the user.

In one embodiment of the disclosure, the controller may include an audio device that indicates to the user that the delivery of suction, fluids and/or energy should be halted or adjusted, for example. Such an audio device may be, for example, a speaker that broadcasts a sound (for example, a beep) that increases in intensity, frequency or tone as a parameter sensed by a sensor increases. The user may adjust, for example, turn down or turn off power supply when the sound emitted reaches a given volume or level. In another embodiment, the audio device may also give an audible signal (such as the message "turn off energy source"), for example, when a parameter sensed by a sensor reaches a certain level. Such an audio device may be located on a valve replacement device, a valve repair device, a power supply, a tissue-engaging device, a suction source, a fluid source, a sensor and/or an imaging device, for example. In one embodiment of the disclosure, the audio device may be a separate device.

In one embodiment of the disclosure, a valve replacement device, a valve repair device, an imaging device, tissue-engaging device, a nerve stimulation device, a cardiac stimulation device, a suction, source, a fluid source, one or more sensors, a drug delivery device, a guidance device and/or a controller may be slaved to a robotic system or a robotic system may be slaved to a valve replacement device, a valve repair device, an imaging device, tissue-engaging device, a nerve stimulation device, a cardiac stimulation device, a suction, source, a fluid source, one or more sensors, a drug delivery device, a guidance device and/or a controller. Computer- and voice-controlled robotic systems that position and maneuver endoscopes and/or other surgical instruments for performing microsurgical procedures through small incisions may be used by the physician or surgeon to perform precise and delicate maneuvers. These robotic systems may allow the surgeon to perform a variety of microsurgical procedures. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

A medical procedure, e.g., a valve repair procedure, a valve replacement procedure, or a valve imaging procedure, of the present disclosure may be non-invasive, minimally invasive and/or invasive. The medical procedure may entail a port-access approach, a partially or totally endoscopic approach, a sternotomy approach or a thoracotomy approach. The medical procedure may include the use of various robotic or imaging systems. The medical procedure may be surgery on the heart. The medical procedure may be a valve procedure. Alternatively, the medical procedure may be surgery performed on another organ of the body.

In one embodiment of the present disclosure, a positioning or tissue-engaging device may comprise one or more sensors and/or electrodes, e.g., sensing electrodes and/or stimulation electrodes. In another embodiment of the present disclosure, an imaging device may comprise one or more sensors and/or electrodes, e.g., sensing electrodes and/or stimulation electrodes. In another embodiment of the present disclosure, a positioning or tissue-engaging device may comprise imaging capabilities, e.g., ultrasound imaging, and one or more sensors and/or electrodes, e.g., sensing electrodes and/or stimulation electrodes.

In one embodiment of the present disclosure, a valve replacement device or system or a valve repair device or system may comprise one or more sensors and/or electrodes, e.g., sensing electrodes and/or stimulation electrodes. In another embodiment of the present disclosure, a valve replacement device or system or a valve repair device or system may comprise imaging capabilities, e.g., ultrasound imaging, and/or one or more electrodes, e.g., stimulation electrodes. In another embodiment of the present disclosure, a valve replacement device or system or a valve repair device or system may comprise tissue-positioning capabilities, e.g., suction engagement of tissue. In one embodiment of the disclosure, a valve replacement device or system or a valve repair device or system may be guided or steerable.

In one embodiment of the present disclosure, devices, systems, and methods that may be used for guidance of a medical device, e.g., a valve replacement device or a valve repair device, in a minimally invasive medical procedure, include electromagnetic devices, systems and methods, electric field devices, systems and methods, and ultrasound devices, systems and methods. Examples of various tracking, monitoring, positioning, guiding and/or navigating technologies are disclosed in U.S. Pat. Nos. 5,782,765; 6,190,395; 6,235,038; 6,379,302; 6,381,485; 6,402,762; 6,434,507; 6,474,341; 6,493,573; 6,636,757; 6,669,635; 6,701,179; 6,725,080, the entire disclosures of which are incorporated herein by reference.

A guidance device, system, and/or method that may be used according to one embodiment of the disclosure include the use of electrical fields, for example, electric fields passing in three axes through a patient's body. In one embodiment, three pairs of sensors, e.g., electrode patches, are positioned in electrical contact with the patient's body. In one embodiment, one set of the electrode patch sensors are oriented in each of the three axes, side-to-side, front-to-back, and head-to-toe, e.g., electrode patch sensors located on neck and thigh. A 40.1 KHz, 40.2 KHz, and 40.3 KHz signal is transmitted, for example, between each of the three sets of electrode patch sensors, respectively. The three signals transmitted between the electrode patch sensors, may be picked up by sensors, e.g., electrodes, positioned on medical devices placed within the patient's body, e.g., within the patient's cardiovascular system or thoracic cavity. Sensor electrodes that are in contact with electrically conductive tissue and/or fluids, e.g., blood, may be monitored from outside of the body via the three signals transmitted between the three pairs of electrode patch sensors, since there will be a voltage drop across each of the three inter-patch spaces within the body associated with electrodes of the medical devices. The voltage drop may be used to calculate the location of the monitored sensor electrode(s) in 3-D space within the patient's body. One embodiment of an electric field guidance device may track the position of up to 10 sensor electrodes simultaneously. An electric field guidance device or system may include a visual monitor or display to display electrode locations or positions. For example, the monitored sensor electrodes may be shown on a three axis coordinate grid on a monitor or display. In one embodiment, the electric field guidance device achieves the best accuracy when the electric field gradients are uniform. Distortions to the electric fields may cause inaccuracies in the rendered position of the electrodes. Electric field distortions may be caused by air voids, for example, within the thoracic cavity. Therefore, sensor electrodes that are being tracked should maintain contact with conductive tissue and/or fluids to have their positions monitored continuously, for example, on the coordinate system.

A guidance device, system, and/or method may use one or more imaging devices to acquire images, for example, previously acquired ultrasound, CT, MRI, PET, fluoroscopy and/or echocardiography images, to provide real-time medical device monitoring, positioning, tracking and/or guidance. Previously acquired images may be registered to the patient. For example, acquired images of anatomical structures of the patient may be accurately registered to the patient's anatomy in real-time. The guidance device or system may then show, for example, on a visual monitor or display, the locations or positions of the medical device sensors relative to a previously acquired image or images, thereby providing real-time monitoring, positioning, tracking and/or guidance of the medical device or devices relative to an image or images of the patient's anatomy.

A guidance device, system, and method that may be used according to one embodiment of the disclosure include the use of a magnetic field. In one embodiment, sensors comprising three small coils are positioned and oriented in three different axes of a medical device, e.g., a valve replacement device or system or a valve repair device or system, and a sensor, e.g., an antenna pad, is placed in contact with the patient's body, for example, the antenna sensor pad is placed under the patient. The magnetic field guidance device and method senses the 3-D location of the three sensor coils of the medical device. The 3-D location of the sensor coils may then be displayed or represented on a visual monitor or display, for example, as shown on a three axis coordinate grid. Again, the guidance device, system, and/or method may use one or more imaging devices to acquire images to provide real-time medical device monitoring, positioning, tracking and/or guidance. For example, a device comprising sensor coils may be monitored as the portion of the device comprising the sensor coils is moved around a space, cavity or chamber, e.g., a cardiac chamber, within the patient. The geometry of the space, cavity or chamber may then be mapped and displayed, for example, on a visual monitor or display. The accuracy of the geometric mapping of a space, cavity or chamber is generally related to the number of data points collected or monitored. A magnetic field guidance device or system is generally not sensitive to air voids within the patient's body.

A guidance device and method that may be used according to one embodiment of the disclosure includes the use of ultrasound. In one embodiment, sensors comprising ultrasound transducers are incorporated into a medical device, e.g., a valve replacement device or system or a valve repair device or system. The ultrasound transducer sensors of the medical device to be tracked emit ultrasonic energy. The ultrasonic energy is then received by ultrasonic transducer sensors on other devices within the patient's body or in contact with the patient's body. The ultrasound guidance device may then display the relative positions of one or more of the ultrasound transducer sensors and renders images of the devices incorporating the ultrasound transducer sensors. Again, the guidance device, system, and/or method may use one or more imaging devices to acquire images to provide real-time medical device monitoring, positioning, tracking and/or guidance. The 3-D location of the ultrasound transducer sensors may be displayed or represented on a visual monitor or display, for example, as shown on a three axis coordinate, grid layered onto a previously acquired image. The ultrasound guidance device or system can be very sensitive to air voids or differences in the speed of sound within various types of tissues and/or fluids.

A guidance device, system, and method that may be used according to one embodiment of the disclosure include the use of an electromagnetic field transmitter that may be coupled to an image intensifier of a fluoroscopic imaging device, e.g., a fluoroscope. In one embodiment, the guidance device or system may transmit three alternating magnetic fields that may be received by coils within the field of interest. The electromagnetic field transmitter may contain a matrix of small metal spheres that may be used to normalize a fluoroscopic image. In one embodiment, fluoroscopic images are acquired in one or more directional orientations using a fluoroscopic imaging device or system. The acquired images are then viewed by a physician who is then able to track and guide a medical device within the field of interest. In one embodiment, each medical device tracked and/or guided comprises at least one receiving sensor coil that allows the medical device to which it is attached to be tracked in 3D space with respect to the previously acquired fluoroscopic image or images.

In embodiment of the present disclosure, previously acquired images, e.g., images of a patient's thoracic cavity, acquired by one or more imaging devices may be displayed while displaying images and precise locations of one or more medical devices inserted into the patient, e.g., the patient's thoracic cavity. The medical devices may be hand held, manually controlled, remotely controlled, e.g., by magnetic fields, and/or robotically controlled. Each medical device that is to be tracked in real-time comprises at least one sensor coil. In one embodiment, electromagnetic navigation or guidance technology utilizes a system that transmits three separate electromagnetic fields that are sensed by a single sensor coil or multiple sensor coils mounted on the medical device to be tracked. In one embodiment, each medical device to be monitored and/or tracked in 3-D space requires at least one sensor coil. Additional medical device sensor coils may provide details regarding the shape and/or path of the medical device, for example. The shape of a flexible and/or articulating portion of a medical device may be provided via sensor coils positioned on or within the flexible and/or articulating portion. For example, an elongated flexible member of a medical device may have multiple sensor coils positioned along its length. In one embodiment, accurate registration of a previously acquired anatomical image may be performed using surface fiducial registration points as well as internal, implanted and/or indwelling reference devices. The form of reference points required to register the image to the true anatomy may depend on the accuracy needed for the particular procedure and anatomy of interest. In terms of information management to the physician or surgeon, one embodiment of this disclosure couples visual imaging, e.g., endoscopic imaging, with navigation or guidance through the virtual anatomy.

One embodiment of the present disclosure involves first imaging of the patient's area of interest, e.g., the patient's thoracic cavity anatomy, using, for example, one or more plane fluoroscopy, computed tomography (CT), magnetic resonance (MR) imaging, and/or one or more plane 2-D or 3-D ultrasound imaging prior to the procedure. The initial imaging may be carried out by first placing fiduciary markers on specific points on or in the patient's body. The fiduciary markers may be easily identified on the images via use of one or more contrast agents or materials identifiable to the particular imaging technique used. The fiduciary markers may be attached to the skin, positioned subcutaneously, implanted, positioned in the trachea, bronchi, and/or esophagus, or may be inserted into the cardiovascular system, for example. In one embodiment, a medical device, e.g., a catheter or catheter-like device, having multiple sensor coils may be placed through the venous system through the inferior vena cava and/or superior vena cava and extended into various additional portions of the right side of the heart, e.g., the right atrial appendage, the coronary sinus, the right ventricle, the inter-ventricular septum, the right ventricular apex, the right ventricular outflow tract, and/or the pulmonary arteries. In one embodiment, delivery to sites such as the pulmonary arteries may be aided by the addition of a balloon positioned at or near the distal end of the fiduciary marking device to make use of blood flow to force the device downstream into the distal end of the right side of the cardiovascular system and into one or more of the pulmonary arteries. Additionally, such a fiduciary marking device may be placed in the arterial side of the cardiovascular system, whereby it may be introduced via an artery into the ascending aorta and extended through the descending aorta (or into superior arterial vessels) and into the aortic valve, the left ventricle, the inter-ventricular septum, the left ventricular apex, the mitral valve annulus, the left atrium, the left atrial appendage, and/or the pulmonary veins. In one embodiment, on or more fiduciary devices inserted into the esophagus and/or trachea may be used to track in-real time respiration effects on the posterior aspects of the heart. One or more reference sensor coils or marking points may be incorporated into a tracheal tube used for a patient on a respirator. One or more reference sensor coils or marking points may be incorporated into an esophageal tube. An esophageal reference may provide information of the location or position of the esophagus during procedures.

In one embodiment, the guidance device or system may include one or more fiducial marking and/or reference devices. The fiducial marking and reference devices may be placed, for example, in and around the heart, e.g., endocardially, epicardially and/or in the pericardial space, to define the real-time precise location of the heart's surfaces and structures. An imaging device may be used to perform an imaging technique while one or more fiduciary marking and reference devices are positioned at one or more locations. Imaging may be performed with regard to respiration and/or cardiac cycle of the patient, such that the motions associated with respiration and/or the beating of the heart may be accounted for during the timing of the acquisition of the images. Placement of fiduciary marking and reference devices may be determined by the physician according to the anatomy of interest where the highest accuracy of the medical devices with respect to the anatomical structures is required. Placements of fiduciary marking and reference devices may be performed using fluoroscopy.

In one embodiment, the guidance device or system may be used during a heart valve replacement or repair procedure. For example, a pulmonic valve replacement procedure using a transvascular approach may involve preliminary imaging with an imaging device, wherein imaging is performed with skin surface fiduciary markers and a fiduciary marking catheter device placed through the venous system into the right ventricular outflow tract and to the site of the pulmonic valve annulus. After the preliminary imaging is complete and the patient is in the operating room, the pre-acquired image is then registered to the patient using the surface fiduciary markers as well as the internal catheter to provide high accuracy in the region of critical interest at the pulmonic valve annulus. The fiduciary catheter device may then be removed and a valve delivery and deployment device may be advanced into the site of the pulmonic valve for delivery and deployment of a replacement valve. During valve delivery and deployment, a physician may use the image guidance navigation device or system to view the real-time location and advancement of the valve delivery and deployment device and to view its motion through the cardiovascular system all the way to the site of deployment at the pulmonic valve annulus, for example.

In one embodiment, the guidance device or system may be used during a minimally invasive procedure or a transcatheter procedure. In one embodiment of the present disclosure, the procedure may be performed from the right side of the patient or the left side of the patient. One or more structures that may be of interest to a physician or surgeon upon entry into a patient's thoracic cavity, e.g., entry through a small incision or port access, may be the location of the pericardial sac and associated structures such as the phrenic nerve. Also of interest may be the location and courses of the caval veins, i.e., the inferior and superior vena cava, the pulmonary arteries, and/or the pulmonary veins. In one embodiment, the caval veins and other structures may be registered to one or more pre-acquired images using fiducial marking devices placed in the venous cardiovascular system. In one embodiment, the pericardial reflections that are located between the superior pulmonary veins are separated. In this region, a surgeon must be careful to avoid damage to the atrial walls, pulmonary veins, and in particular, the pulmonary arteries. Therefore, it may be advantageous to place a fiduciary marking device into one or more of the pulmonary arteries to ensure precise registration of these structures upon start of the procedure in the operating room. Such precise location registration may greatly aid the surgeon in performance of the dissections of these pericardial reflections. In one embodiment, the location of the lung surface may be of interest. In one embodiment, the tracking of the lung surface may be performed via placement of one or more devices comprising one or more tracking sensor coils on the surface of the lung. In one embodiment, an imaging device, e.g., an endoscopic camera and/or light guide, may be used to allow visual imaging of the surgical site or sites. The imaging device may be used to produce one or more images that may be displayed on a monitor. The one or more images may be coupled with the visual display produced from a guidance or navigation device or system. The imaging device may comprise one or more sensor coils, thereby allowing at least a portion of the imaging device to be tracked and/or guided in 3-D space by the guidance or navigation device or system. The visual display produced by the guidance device may be coupled in an appropriate manner to the visual display produced by the imaging device, thereby providing a physician with real-time monitoring of the imaging device and, thereby providing additional information to allow the physician to easily identify anatomical structures located in the viewing area of the imaging device. In one embodiment, imaging devices may be equipped with one or more sensor coils of a guidance system, thereby allowing distal and proximal portions to be identified easily. For example, flexible and/or deflectable medical devices may require multiple sensors, e.g., sensor coils, to define the location and path of multiple portions of the medical device, e.g., the proximal and distal portions of a flexible and/or deflectable distal medical device.

In one embodiment, sensors may be incorporated in one or more medical devices. A sensor may be attached or coupled directly to the surface of a medical device. A sensor may be incorporated into a medical device. A sensor may be incorporated into a removable sheath, cover or insert that may be placed over or inserted into at least a portion of a medical device. A removable sensor sheath, cover or insert may be disposable or re-useable. A sheath or cover may serve to protect one or more portions of a medical device from one or more body fluids and/or tissues. A sheath or cover may comprise one or more lumens that allow suction, irrigation, and/or passage of guide-wires, catheters or similar flexible, and/or polymeric devices through the sheath and into the working region at the distal end of the medical device.

In one embodiment, the guidance device or system may be used during a procedure of guiding, delivery and placement of a valve bioprosthesis or guiding, delivery and repair of a valve. In one embodiment, an imaging device or system may be used to acquire a detailed CT or MRI scan of one or more cardiac structures, for example, one or more valves. In one embodiment, an imaging device or system may be used to acquire a detailed CT or MRI scan of one or more arteries, for example, the carotid, brachiocephalic trunk, subclavian, bronchial, phrenic, hepatic, cephalic trunk, splenic, mesenteric, renal, lumbar, and iliac arteries. It can be important to identify these branch arteries and their locations prior to a particular medical procedure so as to not to occlude any of them during the medical procedure. In one embodiment, the valve replacement delivery device or valve repair delivery device may be equipped with one or more sensor coils to allow precise tracking and guidance of the delivery system through the aortic anatomy. A previously acquired image may be critical in determining the optimal valve placement or repair site.

In one embodiment of the disclosure, one or more images of a patient's anatomy may be produced using one or more imaging device, e.g., an x-ray device, a fluoroscopy device, a CT device, a MRI device, a PET device and/or an ultrasound imaging device. These images may be used in combination with tracked positions of one or more medical devices placed in a patient. These medical devices, e.g., a valve replacement device or a valve repair device, may be tracked using one or more guidance devices comprising, for example, one or more sensors. The medical devices may also comprise one or more sensors. In one embodiment of the disclosure, a computer generated display showing a medical device's position created by a guidance device or system may be superimposed on a previously acquired image or images produced by one or more imaging devices. In one embodiment of the disclosure, a guidance device or system may include one or more imaging devices. In one embodiment of the disclosure, a guidance device or system may include a controller, e.g., a controller as discussed above. In one embodiment of the disclosure, a guidance device or system may include one or more sensors, e.g., wherein the sensors are coupled to a controller. In one embodiment of the disclosure, a guidance device or system may be slaved to a robotic system or a robotic system may be slaved to a guidance device or system.

In one embodiment of the disclosure, a method of real-time image registration includes monitoring in real-time fixed surface and indwelling fiduciary marking devices so as to update and correct the registration of previously acquired images, e.g., x-ray images, fluoroscopy images, CT images, MRI images, PET images and/or ultrasound images, thereby providing real-time changes in position of the anatomical structures of interest, e.g., respiration, cardiac motion, and intestinal peristalsis.

In one embodiment of the disclosure, a guidance device or system may comprise an electrical sensor, a magnetic field sensor, an optical sensor, an acoustic sensor and/or an inertial sensor. In one embodiment of the disclosure, a guidance device or system may comprise a magnetic field generator. In one embodiment of the disclosure, a sensor coil may comprise an electrically conductive, magnetically sensitive element that may be responsive to time-varying magnetic fields for generating induced voltage signals as a function of, and representative of, the applied time-varying magnetic field.

One embodiment of the disclosure comprises a valve replacement device or valve repair device and one or more sensors, e.g., receiving sensor coils that allow electromagnetic tracking and navigation in 3-D space of the location of one or more portions of the devices. In one embodiment of the disclosure, the valve replacement device is a valve replacement delivery device or system. In one embodiment of the disclosure, the valve replacement device is a replacement valve. In one embodiment of the disclosure, the valve repair device is a valve repair delivery device or system. In one embodiment of the disclosure, the valve repair device is an implantable valve repair device. In one embodiment of the disclosure, the valve replacement device or valve repair device is a surgical device. In one embodiment of the disclosure, the valve replacement device or valve repair device is a minimally invasive device and/or an endoscopic device. In one embodiment of the disclosure, the valve replacement device or valve repair device is a transcatheter device. In one embodiment of the disclosure, the valve replacement device or valve repair device comprises one or more portions that are flexible, articulating, malleable and/or rigid.

One embodiment of the disclosure includes one or more fiduciary marking or reference devices that may be used to update and correct the registration of previously acquired images, e.g., x-ray images, fluoroscopy images, CT images, MRI images, PET images and/or ultrasound images, thereby providing real-time changes in position of the anatomical structures of interest, e.g., respiration, cardiac motion, and intestinal peristalsis. In one embodiment, a fiduciary marking or reference device is visualizable and/or detectable by one or more means of non-invasive imaging such as x-ray, fluoroscopy, computed tomography, magnetic resonance, PET and/or ultrasound imaging. In one embodiment, the fiduciary marking or reference device may include one or more sensors, e.g., sensor coils, thereby allowing the device's location in 3-D space to be easily determined and used as a reference and/or real-time registration point or points for tracking, navigation and/or guidance, e.g., electromagnetic tracking, navigation and/or guidance, in 3-D space.

One embodiment of the disclosure includes a fiduciary reference or marking device which may be fixed in location on or within a patient's body via an adhesive, a tissue fixation screw, helix, barb and/or hook, a suction source, an inflatable balloon, an expandable structure, and/or via physical pressure.

One embodiment of the disclosure includes an esophageal device that comprises one or more sensors, e.g., receiving sensor coils, which allow determination of the location of the esophageal device in 3-D space. One embodiment of the disclosure includes a trans-esophageal device, e.g., a trans-esophageal imaging device and/or a trans-esophageal stimulation device, which comprises one or more sensors, e.g., receiving sensor coils, which allow determination of the location of the trans-esophageal device in 3-D space.

One embodiment of the disclosure includes a tracheal device that comprises one or more sensors, e.g., receiving sensor coils, which allow determination of the location of the tracheal device in 3-D space. One embodiment of the disclosure includes a trans-tracheal device, e.g., a trans-tracheal imaging device and/or a trans-tracheal stimulation device, which comprises one or more sensors, e.g., receiving sensor coils, which allow determination of the location of the trans-tracheal device in 3-D space.

One embodiment of the disclosure includes a vascular device that comprises one or more sensors, e.g., receiving sensor coils, which allow determination of the location of the vascular device in 3-D space. One embodiment of the disclosure includes a trans-vascular device, e.g., a trans-vascular imaging device, a trans-vascular stimulation device, a trans-vascular valve replacement device and/or a trans-vascular valve repair device, which comprises one or more sensors, e.g., receiving sensor coils, which allow determination of the location of the trans-vascular device in 3-D space.

One embodiment of the disclosure includes a guiding device, e.g., a guiding catheter device, which comprises one or more sensors, e.g., receiving sensor coils, which allow determination of the location of the guiding device in 3-D space. One embodiment of the disclosure includes a catheter-like insert device, which may be inserted through the lumen of a larger catheter device, the catheter-like insert device comprising one or more sensors, e.g., receiving sensor coils, which allow determination of the location of the catheter-like insert device in 3-D space.

One embodiment of the disclosure includes a stimulation device that comprises one or more sensors, e.g., receiving sensor coils, which allow determination of the location of the stimulation device in 3-D space. One embodiment of the disclosure includes a nerve stimulation device, e.g., a vagal nerve stimulation device, which comprises one or more sensors, e.g., receiving sensor coils, which allow determination of the location of the nerve stimulation device in 3-D space.

One embodiment of the present disclosure includes a tissue-engaging device that comprises one or more sensors, e.g., receiving sensor coils, which allow determination of the location of the tissue-engaging device in 3-D space. One embodiment of the present disclosure includes a tissue dissection device, which comprises one or more sensors, e.g., receiving sensor coils, which allow determination of the location of the tissue dissection device in 3-D space. One embodiment of the disclosure includes a tissue retraction device, which comprises one or more sensors, e.g., receiving sensor coils, which allow determination of the location of the tissue retraction device in 3-D space.

One embodiment of the disclosure includes a valve replacement device or system that comprises one or more sensors, e.g., receiving sensor coils, which allow determination of the location of the valve replacement device or system in 3-D space. One embodiment of the disclosure includes a valve replacement delivery device or system that comprises one or more sensors, e.g., receiving sensor coils, which allow determination of the location of the valve replacement delivery device or system in 3-D space.

One embodiment of the disclosure includes a valve repair device or system that comprises one or more sensors, e.g., receiving sensor coils, which allow determination of the location of the valve repair device or system in 3-D space.

One embodiment of the disclosure includes a valve repair delivery device or system that comprises one or more sensors, e.g., receiving sensor coils, which allow determination of the location of the valve repair delivery device or system in 3-D space.

A medical procedure according to one embodiment of the present disclosure may be a non-invasive, minimally invasive and/or invasive procedure. In one embodiment, the medical procedure may entail a port-access approach, a partially or totally endoscopic approach, a sub-xyphoid approach, a sternotomy approach and/or a thoracotomy approach. In one embodiment, the medical procedure may entail a trans-vascular procedure, a percutaneous procedure and/or a transcatheter procedure. The medical procedure may include the use of various robotic, imaging systems, and/or guidance systems. The medical procedure may be a procedure comprising the heart, e.g., valve replacement and/or valve repair. Alternatively, the medical procedure may be a procedure comprising another organ of the body. The medical procedure may be a procedure comprising more than one organ of the body. In one embodiment, on or more medical devices of the present disclosure may be positioned and used, for example, through a sternotomy, through a thoracotomy that avoids the sternal splitting incision of conventional cardiac surgery, through a mini-thoracotomy, through a sub-xyphoid incision, percutaneously, trans-venously, arthroscopically, endoscopically, for example, through a percutaneous port, through a stab wound or puncture, through a small or large incision, for example, in the chest, in the groin, in the abdomen, in the neck or in the knee, or in combinations thereof. In one embodiment, on or more medical devices of the present disclosure may be guided into a desired position using various imaging and/or guidance techniques as described herein.

Figure 13:
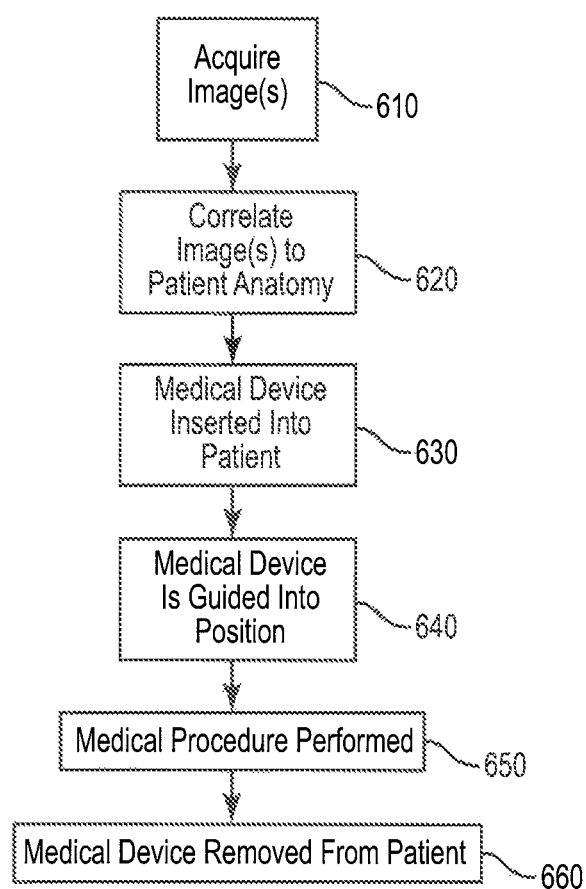
FIG. 13 is a flow diagram of one embodiment of the disclosure.

One embodiment of a method according to the present disclosure is outlined in FIG. 13. An imaging device acquires one or more images, as described herein, of a patient's anatomy of interest at 610. Next an image guidance system comprising reference markers, as described herein, is used to correlate the acquired image(s) with the patient's anatomy at 620. A medical device, e.g., a valve replacement device or system and/or a valve repair device or system, comprising one or more image guidance sensors is then inserted into the patient at 630. The medical device is then guided into a desired position, e.g., adjacent cardiac tissue, using the image guidance system at 640. A medical procedure, e.g., a valve replacement procedure or a valve repair procedure comprising the replacement of a cardiac valve or repair of a cardiac, is performed at 650. The medical device, or a portion thereof, is removed from the patient at 660.

Figure 14:
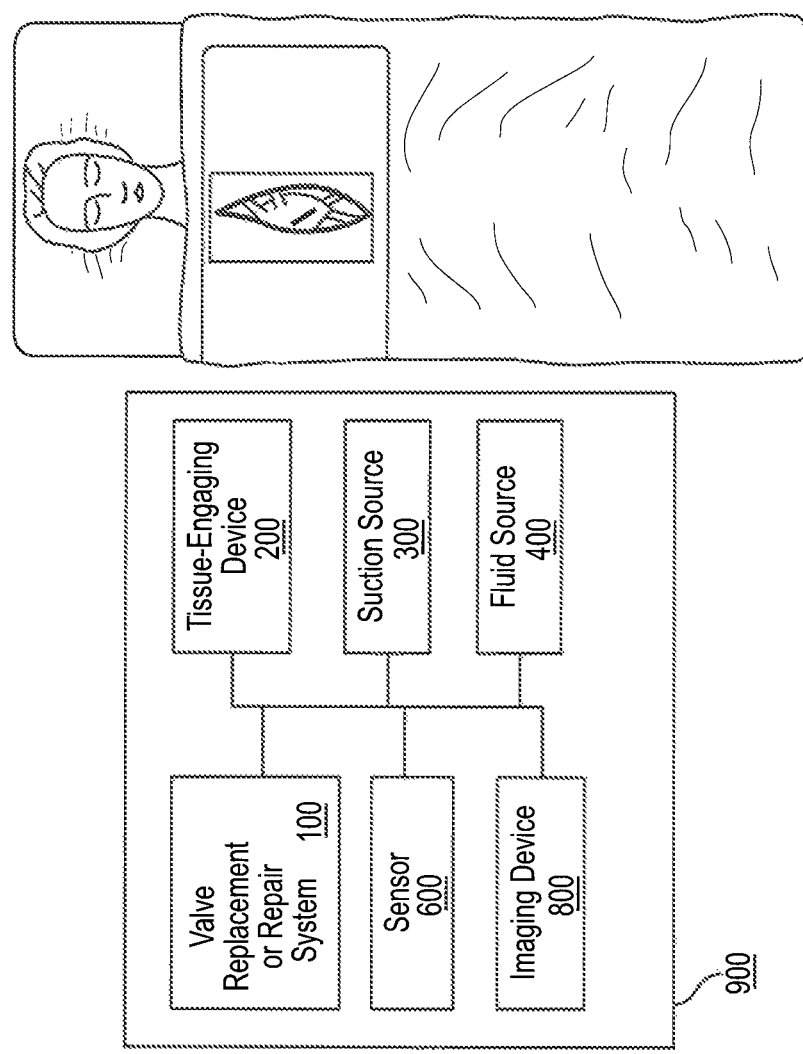
FIG. 14 is a schematic view of one embodiment of a system in accordance with the disclosure.

FIG. 14 shows a schematic view of one embodiment of a system 900 for replacing or repair one or more cardiac valves. In this embodiment, system 900 is shown to comprise a valve replacement or repair system 100, a tissue-engaging device 200, a suction source 300, a fluid source 400, a sensor 600 and an imaging device 800. The valve replacement or repair system 100 may include a valve replacement delivery device or system or a valve repair delivery device or system. In one embodiment of the disclosure, the valve replacement or repair delivery systems may comprise a power supply and/or a controller. System 900 may also include a drug delivery device, a guidance device, a nerve stimulation device and/or cardiac stimulation device (all not shown in FIG. 14). The tissue-engaging device may comprise one or more suction or vacuum ports, openings, orifices, channels or elements positioned on, along, within or adjacent a tissue contact surface. The suction ports, openings, orifices, channels or elements may communicate suction through the tissue contact surface to the atmosphere to engage or grasp tissue via suction. In one embodiment of the disclosure, the tissue-engaging device may be used to position, manipulate, hold, grasp, immobilize and/or stabilize tissue in accordance with the present disclosure. The drug delivery device may be used to deliver drugs and/or biological agents to a patient. The imaging device may be used to image or illuminate a tissue site. The imaging and guidance devices may be used to help control and guide one or more components of system 900 during a medical procedure. In one embodiment of the disclosure, a valve replacement device or system or a valve repair device or system may comprise a tissue-engaging device.

The present disclosure has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the disclosure. Thus, the scope of the present disclosure should not be limited to the structures described herein. Further, it will be appreciated by those skilled in the art that while the disclosure has been described above in connection with particular embodiments and examples, the disclosure is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference in its entirety, as if each such patent or publication were individually incorporated by reference herein.

What is claimed is:

1. A method for determining whether a replacement heart valve is appropriate for implanting in a section of a heart of a patient into which the replacement heart valve is to be implanted, the method comprising:
    inserting an expandable distal end portion of a sizing device into the section of the heart of the patient into which the replacement heart valve is to be implanted, wherein selective expansion of the distal end portion of the sizing device applies a selected radial force to the section of the heart, wherein the selective expansion of the distal end portion simulates at least one property of the replacement heart valve in a deployed state;
    imaging the section of the heart while the distal end portion of the sizing device in an expanded state applies a radial force to the section of the heart during heart rhythm; and
    reimaging the section of the heart while the distal end portion of the sizing device in a contracted state does not apply the radial force to the section of the heart during heart rhythm;
    deriving, from the imaging and the reimaging, dimensional characteristics of the section of the heart based on images of the distal end portion of the sizing device applying and not applying the radial force to the section of the heart; and
    determining whether the replacement heart valve is appropriate for implantation in the section of the heart based on the derived dimensional characteristics of the section of the heart.

2. The method of claim 1 wherein inserting the expandable distal end portion of the sizing device into the section of the heart includes inserting the expandable distal end portion of the sizing device into an aortic root.

3. The method of claim 1 comprising allowing blood to flow through the section of the heart of the patient during the imaging and reimaging.

4. The method of claim 3 wherein the allowing blood to flow comprising reducing blood flow through the section of the heart of the patient during the imaging and reimaging.

5. The method of claim 1 wherein determining whether the replacement heart valve is appropriate for implantation includes determining whether no replacement heart valve is appropriate for implantation.

6. The method of claim 5 wherein the expanded state includes a first expanded state applying a first radial force to the section of the hear during heart rhythm and comprising, if no replacement heart valve is appropriate for implantation, applying a second radial force on the section of the heart with the sizing device by selectively expanding the distal end portion of the sizing device to a second expanded state, imaging the section of the heart including the distal end portion of the sizing device in the second expanded state, and reimaging the section of the heart including the distal end portion of the sizing device in the contracted, wherein the second radial force is different than the first radial force.

7. A method for determining an appropriate replacement heart valve for implanting in a heart of a patient, the method comprising:
    inserting an expandable distal end portion of a sizing device into a section of the heart of the patient into which the replacement heart valve is to be implanted, wherein the distal end portion of the sizing device is configured to apply a selected radial force from a variable radial force to the section of the heart;
    imaging the section of the heart including the distal end portion of the sizing device in a selected expanded state during heart rhythm, wherein the distal end portion of the sizing device in the selected expanded state simulates at least one property of a replacement heart valve in a deployed state and the selected expanded state applies a selected radial force to the section of heart;
    reimaging the section of the heart including the distal end portion of the sizing device in a contracted state during heart rhythm;
    deriving, from the imaging and the reimaging, dimensional characteristics of the section of the heart based on images of the distal end portion of the sizing device applying and not applying the selected radial force to the section of the heart; and
    selecting a replacement heart valve for implantation in the section of the heart based on the derived dimensional characteristics.

8. The method of claim 7 wherein selecting the replacement heart valve includes determining a stent height of the replacement heart valve to avoid the coronary ostia.

9. The method of claim 7 wherein the deriving includes determining measurements of the section of the heart and evaluating parameters of the section of the heart.

10. The method of claim 7 wherein the imaging and reimaging are performed with an intraoperative technique.

11. The method of claim 7 wherein deriving dimensional characteristics includes deriving a diameter.

12. The method of claim 7 wherein deriving dimensional characteristics includes deriving circularity.

13. A method for determining whether a heart valve prosthesis is appropriate for implanting in a heart of a patient, comprising:

inserting an expandable distal end portion of a sizing device into a section of the heart of the patient, wherein a selected expansion of the distal end portion of the sizing device applies a selected radial force to the section of the heart of the patient;

imaging the section of the heart of the patient including the distal end portion of the sizing device in a selected expanded state during heart rhythm;

reimaging the section of the heart of the patient including the distal end portion of the sizing device in a selected contracted state during heart rhythm;

deriving, from the imaging and the reimaging, dimensional characteristics of the section of the heart; and determining whether the heart valve prosthesis is appropriate for implantation in the section of the heart based on the selected radial force and the derived dimensional characteristics.

14. The method of claim 13 wherein inserting the expandable distal end portion of the sizing device comprises inserting a balloon.

15. The method of claim 14 wherein inserting the balloon includes one of inserting a compliant balloon and inserting a noncompliant balloon.

16. The method of claim 13 wherein inserting the sizing device includes inserting a sizing device having features detectable during imaging and reimaging.

17. The method of claim 13 comprising removing the sizing device prior to implanting the heart valve prosthesis.

18. The method of claim 13 wherein providing the selected radial force of the sizing device includes providing a selected radial force corresponding with a radial force of the heart valve prosthesis to be deployed at the section of the heart of the patient.

19. The method of claim 13 comprising evaluating, from the imaging and reimaging, parameters of the section of the heart of the patient.

20. The method of claim 19 determining whether the heart valve prosthesis is appropriate for implantation in the section of the heart is further based on the evaluated parameters of the section of the heart of the patient.

21. The method of claim 13 wherein deriving dimensional characteristics includes deriving a diameter.

22. The method of claim 13 wherein deriving dimensional characteristics includes circularity.

* * * * *